(12) United States Patent
Moritake et al.

(10) Patent No.: US 7,500,785 B2
(45) Date of Patent: Mar. 10, 2009

(54) X-RAY SHIELDING DEVICE

(75) Inventors: Takashi Moritake, Chiba (JP); Hiroto Koizumi, Higashi-Ibaraki-gun (JP); Hironobu Ono, Naka-gun (JP)

(73) Assignees: National Institute of Radiological Sciences, Chiba-shi (JP), part intrest; Kanto Giken Co. Ltd., Naka-gun, Ibaraki (JP), part intrest ( * ) Notice: Subject to any disclaimer, the term of this patent is extended or adjusted under 35 U.S.C. 154(b) by 0 days.

(21) Appl. No.: 11/889,516

(22) Filed: Aug. 14, 2007

(65) Prior Publication Data

US 2007/0297572 A1    Dec. 27, 2007

Related U.S. Application Data

(63) Continuation of application No. PCT/JP2006/302761, filed on Feb. 16, 2006.

(30) Foreign Application Priority Data

Feb. 16, 2005    (JP) .............................. 2005-039556

(51) Int. Cl.
*H01J 35/16* (2006.01)
*A61B 6/02* (2006.01)
*G21K 5/10* (2006.01)

(52) U.S. Cl. .......................... 378/203; 378/42; 378/146

(58) Field of Classification Search ................. 378/147, 378/203, 42, 62, 148, 150–153, 205
See application file for complete search history.

(56) References Cited

U.S. PATENT DOCUMENTS

| 5,519,223 | A * | 5/1996 | Hug et al. ................. 250/363.1 |
| 6,501,828 | B1 * | 12/2002 | Popescu ....................... 378/150 |
| 6,618,465 | B2 * | 9/2003 | Mohr et al. .................... 378/58 |

FOREIGN PATENT DOCUMENTS

| JP | 2000-308634 | 11/2000 |
| JP | 2002-025488 | 1/2002 |
| JP | 2004-49849 | 2/2004 |

* cited by examiner

*Primary Examiner*—Edward J Glick
*Assistant Examiner*—Mona M Sanei
(74) *Attorney, Agent, or Firm*—Jacobson Holman PLLC

(57) ABSTRACT

An X-ray shield device according to one embodiment of the present invention comprises an X-ray shielding plate positioned between an X-ray source and a support member for a subject; a shielding plate driving mechanism including a supporting portion for supporting the X-ray shielding plate, the shielding plate driving mechanism being operable to move the shield plate supported by the supporting portion in a movement plane of the shielding plate perpendicular to a path of X-ray irradiation; and an X-ray shielding plate exchanging means for exchanging the X-ray shielding plate supported by the supporting portion for another X-ray shielding plate of different size.

13 Claims, 18 Drawing Sheets of an X-ray source of the X-ray fluoroscopic apparatus may require a temporal interruption of the operation and then a manual repositioning of the shielding disk in place.

X-RAY SHIELDING DEVICE

This is a continuation of PCT/JP06/302761 filed Feb. 16, 2006 and published in Japanese.

BACKGROUND OF THE INVENTION

1. Technical Field

The present invention relates generally to an X-ray shielding device and, more particularly to an X-ray shielding device for preventing a patient from being exposed to a portion of X-ray radiation in an X-ray fluoroscopic apparatus.

2. Background Art

In medical applications, diagnosis based on an X-ray fluoroscopic apparatus has been traditionally carried out. More recently, the X-ray fluoroscopic apparatus has been also used for treatment procedures in addition diagnosis procedures.

It has been common to treat a patient, for example, suffering from cranial aneurysm by open brain surgery under general anesthesia, but, recently, not a few intravascular surgeries may be conducted. The intravascular surgery may be conducted based on a microcatheter which is delivered through a blood vessel, which may involve use of an X-ray fluoroscopic apparatus (an angiographic system). Such an intravascular surgery may conveniently require no large incisions in the human body and be less invasive.

When the X-ray fluoroscopic apparatus is adapted to be used for treatment, however, it can be forced to irradiate the human body with X-ray radiation for relatively longer irradiation time, as compared to diagnosis. Also, X-rays may be emitted to not only a site of the human body requiring the fluoroscopy, but also an adjacent site of the human body requiring no fluoroscopy.

It will be understood that such an undesirable medical exposure of the patient, in particular certain sites of the human body should be reduced or even eliminated as far as possible. Such reduction in the X-ray exposure is very important for some human body site less resistive to radiation, i.e. requiring less exposure dose. For example, in the case of intravascular surgery on the human cranial region or head, the reduction in the exposure of human eyeballs, in particular lenses thereof is absolutely important from the standpoint of prevention of cataract.

Japanese Laid-Open Patent Application No. 2004-49849 discloses an X-ray shielding device used in conjunction with an X-ray fluoroscopic apparatus and intended to reduce the undesirable medical X-ray radiation exposure as mentioned above. The disclosed X-ray shielding device includes a radiation shielding disk made of lead disposed the head of the patient and an X-ray tube of the X-ray fluoroscopic apparatus situated below the patient head. The shielding disk can be translated in an X-Y plane and also tilted at a desired angle about an X axis, which shielding disk may be in turn adapted to be rotated about a Z axis. While the X-ray tube radiates X-rays in the Z axis direction, the X-rays is caused to be continuously shielded by a circular area defined the shielding disk being rotated.

Such conventional X-ray shielding device may require a complex operating mechanism which allows the pivotal and continuous rotating movements of the shielding disk about the X and Z axes, respectively in addition to the translational movement in the X-Y plane thereof.

Typically, the X-ray shielding lead disk may be situated in an upright position or in the Z axis direction. This is not feasible in terms of design considerations because of a limited space between the head of the patient and the X-ray tube of the X-ray fluoroscopic apparatus. In addition, displacement of an X-ray source of the X-ray fluoroscopic apparatus may require a temporal interruption of the operation and then a manual repositioning of the shielding disk in place.

It is an object of the present invention to solve the problems as described above, and to provide an X-ray shielding device for use with an X-ray fluoroscopic apparatus that is adapted to provide a better space-saving configuration and make effective use of a limited space available in a medical environment and also that can be arranged in such a manner to automatically move an X-ray shielding disk in synchronization with movement of the X-ray source to shield a particular site or area of a subject from the X-ray radiation.

In order to the above object, the present invention provides an X-ray shield device for use with an X-ray fluoroscopic apparatus for fluoroscopically visualizing a certain site of a subject, comprising an X-ray generator containing an X-ray source, an X-ray detector associated with the X-ray generator and including a projection plane disposed opposed to the X-ray source, and a support member disposed between the X-ray source and the projection plane independently of the X-ray detector for supporting the subject, the X-ray shield device being adapted to prevent a specified site of the subject from exposure to the X-ray from the X-ray source, said X-ray shield device comprising at least one X-ray shielding plate positioned between the X-ray source and the support member; a shielding plate driving mechanism including a supporting portion for supporting said X-ray shielding plate, said shielding plate driving mechanism being operable to move the shield plate supported by the supporting portion in a direction transverse to a path of X-ray irradiation; and a control unit for controlling operation of said shielding plate driving mechanism to cause it to move said shielding plate in a manner so as to shield said specified site of the subject from the X-ray from the X-ray source of the X-ray generator upon movement of the X-ray generator and the X-ray detector relative to the support member.

In the X-ray shield device according to the present invention, preferably, said supporting portion of the shielding plate driving mechanism is operable to support selected one of said X-ray shielding plates of different sizes for exchange.

In accordance with one aspect of the present invention, preferably, said control unit is operable to move said X-ray shielding plate to a shielding position on which said X-ray shielding plate is to be centered and at which a line extending centrally through the X-ray source and the specified site of the subject to be shielded from the X-ray irradiation from the X-ray source, intersects a plane in which said shielding plate is moved.

In accordance with another aspect of the present invention, preferably, the X-ray shield device also comprises a shielding position determining means for determining said shielding position, said control unit being operable to move said X-ray shielding plate to said shielding position determined by said shielding position determining means.

In accordance with another aspect of the present invention, preferably, said shielding position determining means comprises; a position of X-ray source measuring device for measuring the position of the X-ray source S relative to a common reference point; a position of shielding plate driving mechanism measuring device for measuring the position of the shielding plate driving mechanism relative to said common reference point; a position of non-irradiation site measuring device for measuring the position of said specified site relative to said common reference point; and a computing unit for computing said shielding position based on data from said X-ray source position measuring device, data from said shielding plate driving mechanism position measuring device and data from said non-irradiation position measuring device.

In accordance with still another aspect of the present invention, preferably, said control unit is operable to move said X-ray shielding plate to a shielding position on which said X-ray shielding plate is to be centered and at which a line extending centrally through the X-ray source and a position of an image of the specified site of the subject on a projection plane where the specified site of the subject is projected, intersects a plane in which said shielding plate is moved.

In accordance with still another aspect of the present invention, preferably, the X-ray shield device further comprises a shielding position determining means for determining said shielding position, said control unit being operable to move said X-ray shielding plate to said shielding position determined by said shielding position determining means.

In accordance with another aspect of the present invention, preferably, said shielding position determining means comprises; a position of X-ray source measuring device for measuring the position of the X-ray source relative to a common reference point; a position of shielding plate driving mechanism measuring device for measuring the position of the shielding plate driving mechanism relative to said common reference point; a position of non-irradiation site projection image measuring device for measuring the position of the image of said specified site of the subject that is projected on the projection plane relative to said common reference point; and a computing unit for computing said shielding position based on data from said X-ray source position measuring device, data from said shielding plate driving mechanism position measuring device and data from said non-irradiation site's projection image position measuring device.

In accordance with still another aspect of the present invention, preferably, the X-ray shield device further comprises a shielding plate size determining means for determining a size of said X-ray shielding plate to be placed at said shielding position that is suitable for said specified site of the subject to be shielded from the X-ray irradiation from the X-ray source.

In accordance with another aspect of the present invention, preferably, said shielding plate size determining means comprises; said shielding position determining means, a size of non-irradiation site storing device for storing data relating to the size of a non-irradiation site of the subject projected onto a plane perpendicular to the center line which passes through the X-ray source and the center of the non-irradiation site, and a computing unit for computing the size of the X-ray shielding plate suitable for the non-irradiation site of the subject based on data provided from said shielding position determining means and data provided from said non-irradiation site's size storing device.

In accordance with still further aspect of the present invention, preferably, the X-ray shield device further comprises an X-ray shielding plate exchanging means for exchanging said X-ray shielding plate supported by said supporting portion of the X-ray shielding plate driving mechanism for another X-ray shielding plate of different size.

In accordance with another aspect of the present invention, preferably, said shielding plate exchanging means comprises a shielding plate rack for releasably holding more than one X-ray shielding plates of different sizes; said supporting portion of the X-ray shielding plate driving mechanism is configured to releasably support said X-ray shielding plate; and said X-ray shielding plate driving mechanism is constructed to move the supporting portion thereof in such a manner that the supporting portion is caused to pass the X-ray shielding plate supported thereby onto said shielding plate rack which can hold that X-ray shielding plate and to receive thereon selected one of X-ray shielding plates held by the shielding plate rack.

In accordance with still another aspect of the present invention, preferably, said control unit is operable to control said X-ray shielding plate exchanging means in such a manner that said supporting portion of the X-ray shielding plate driving mechanism is caused to pass the X-ray shielding plate supported thereby onto said shielding plate rack which can hold that X-ray shielding plate and to receive thereon an X-ray shielding plate of X-ray shielding plates held by the shielding plate rack whose size is determined by said shielding plate size determining means.

In accordance with another aspect of the present invention, preferably, said shielding plate driving mechanism is adapted to move the X-ray shielding plate along said path of X-ray irradiation.

In accordance with still another aspect of the present invention, preferably, the X-ray shield device further comprises a command input unit operatively connected to said control unit.

In accordance with another aspect of the present invention, preferably, said X-ray shield device comprising at least two X-ray shielding plates positioned between the X-ray source and the support member in order to prevent a plurality of specified sites of the subject from exposing to the X-ray from the X-ray source, and at least two shielding plate driving mechanism each operable to move the respective X-ray shielding plate, each of said shielding plate driving mechanisms being adapted to move the respective X-ray shielding plate in a direction transverse to a respective path of X-ray irradiation at a different position on said X-ray irradiation path.

As can be appreciated by those skilled in the art, the present invention provides an X-ray shield device having a better space-saving configuration and capable of being arranged in such a manner to automatically move an X-ray shield plate in synchronization with movement of the X-ray source to shield a particular site or area of a subject from the X-ray radiation.

BRIEF DESCRIPTION OF THE DRAWINGS

For the purpose of illustrating the invention, there are shown in the drawings several forms which are presently preferred, it being understood, however, that the invention is not limited to the precise form disclosed.

FIG. 9-1 is a view showing a step in which an X-ray shielding disk is held by an arm at the shielding disk rack;

FIG. 9-2 is a view showing another step in which the X-ray shielding disk is held by the arm at the shielding disk rack;

FIG. 9-3 is a view showing a further step in which the X-ray shielding disk is held by the arm at the shielding disk rack;

BEST MODE FOR CARRYING OUT THE INVENTION

Several embodiments of the present invention will now be described with reference to the accompanying drawings. These embodiments will be discussed in connection with an X-ray fluoroscopic apparatus which may be used with an angiographic system.

Figure 1:
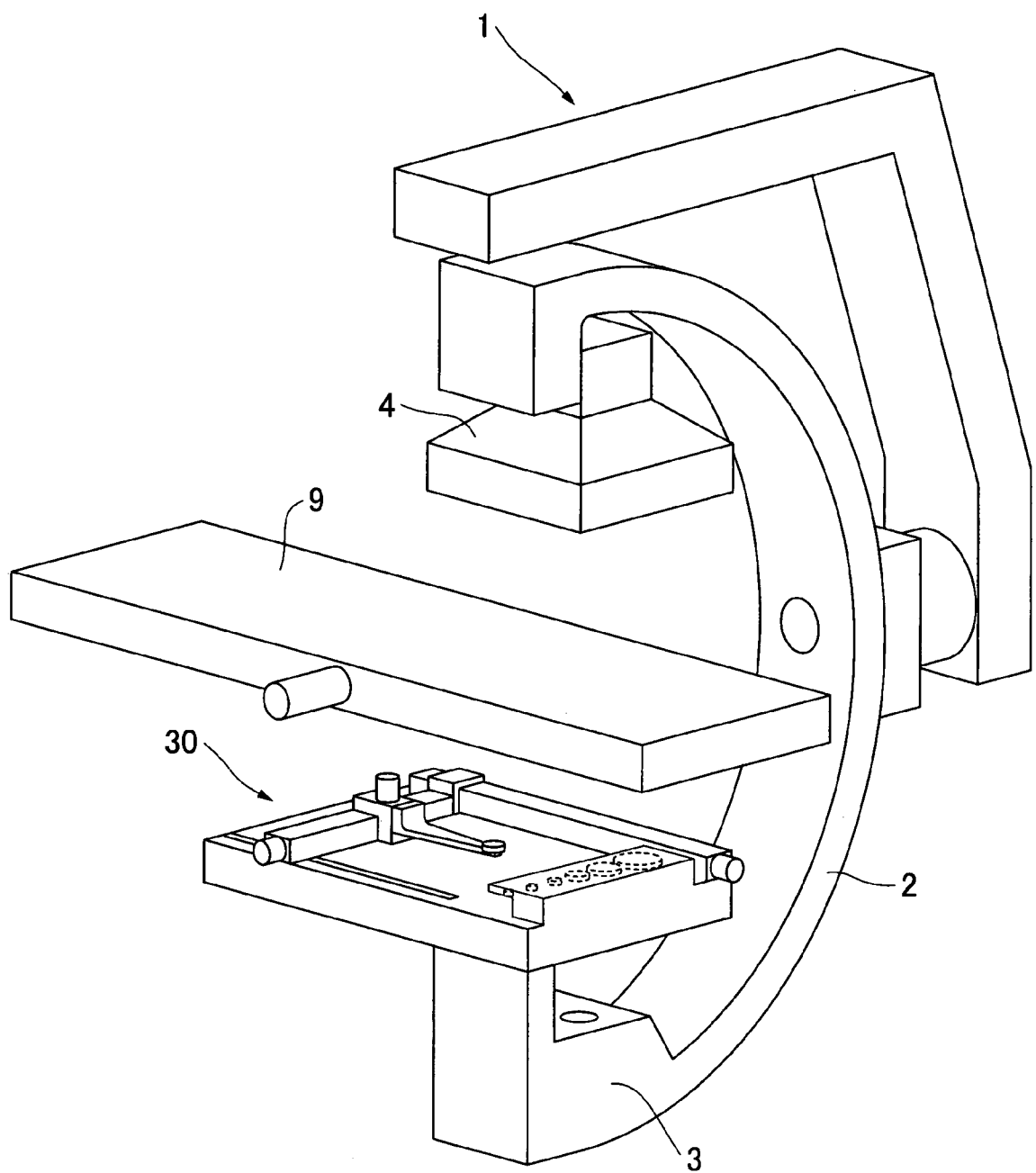
FIG. 1 is a schematically perspective view partially showing an angiographic system.
Figure 2:
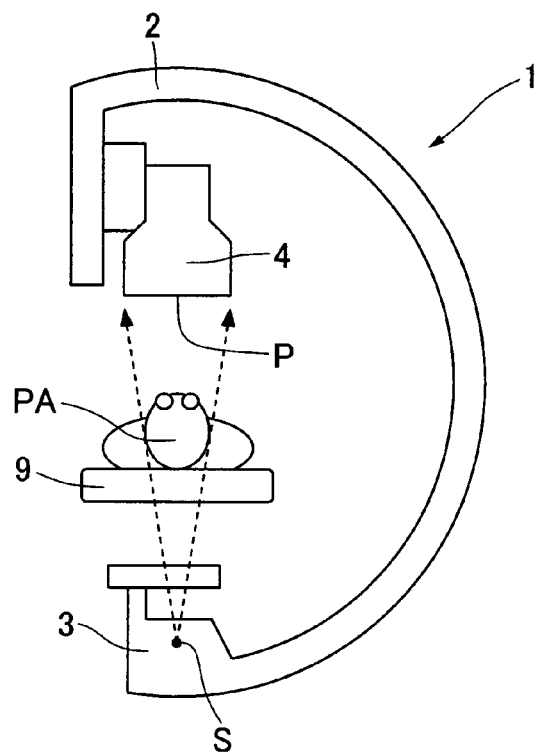
FIG. 2 is a schematic front view partially showing the angiographic system.

Referring to FIGS. 1 and 2, there is schematically shown a known angiographic system generally designated by a reference numeral 1.

This angiographic system 1 has a C-shaped fixed arm 2 which is provided at its bottom end with an X-ray generator 3 which contains an X-ray source S. An X-ray detector 4 is mounted on the top of the arm 2. The X-ray detector 4 comprises a projection plane P disposed opposed to the X-ray source S.

Figure 3:
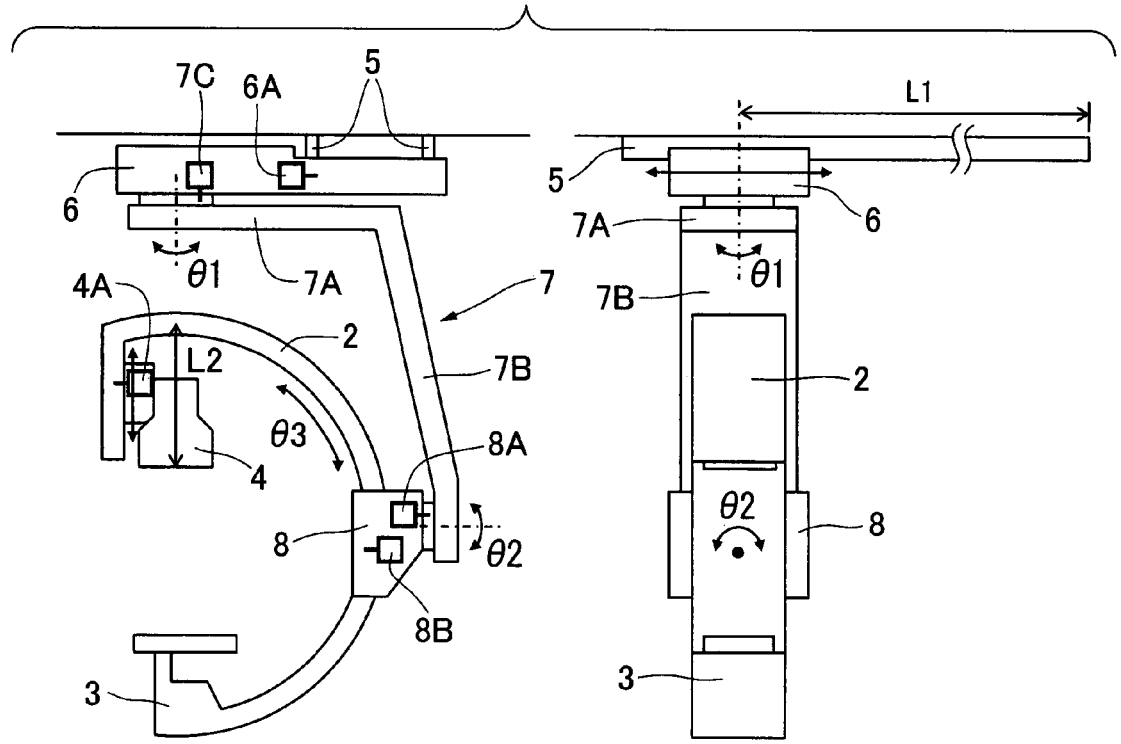
FIG. 3 shows schematic front and left side views of the angiographic system.
Figure 4:
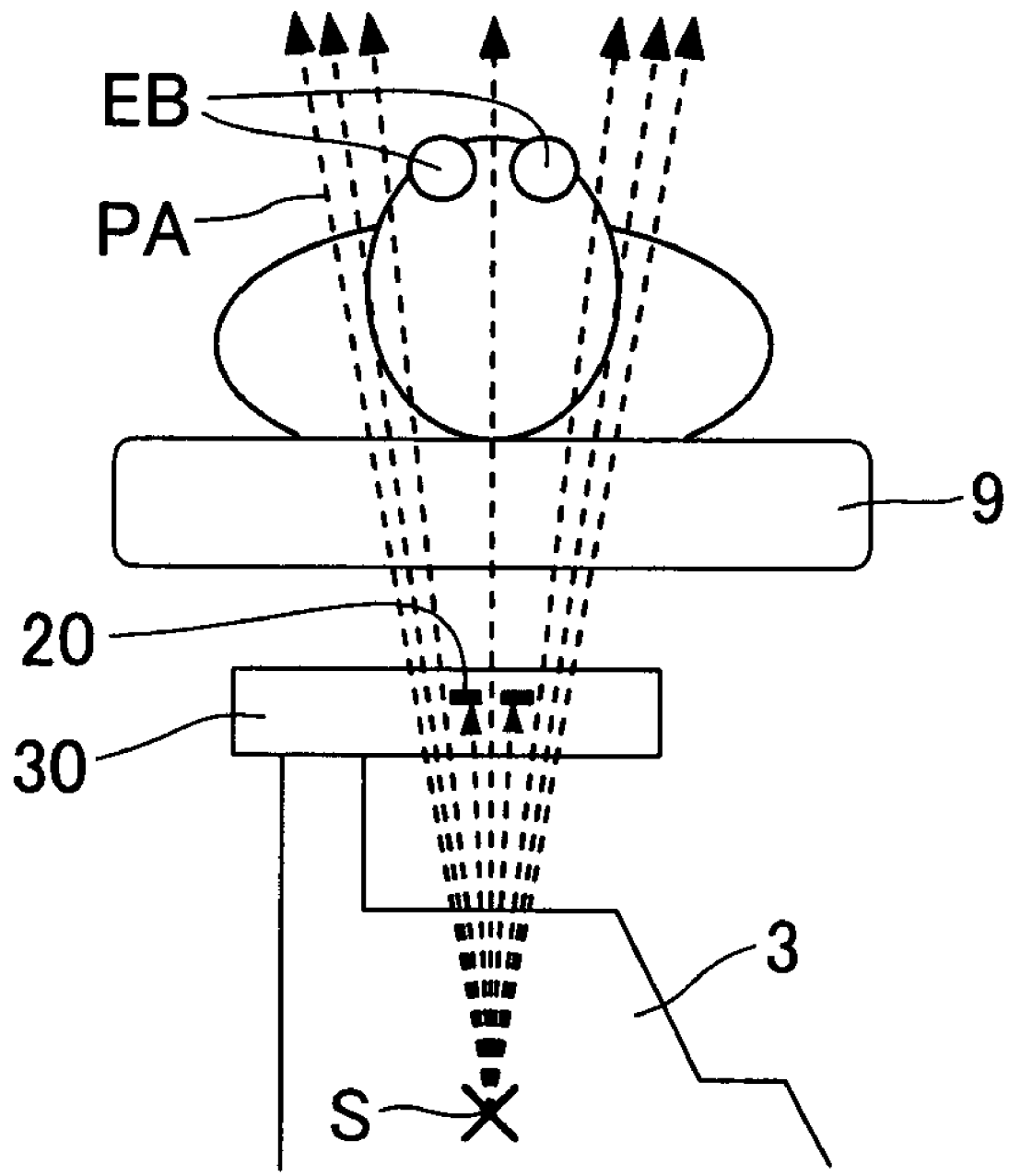
FIG. 4 is a schematic front view partially showing the positional relationship between an X-ray shield device according to the first embodiment of the present invention and an angiographic system.

As shown in FIG. 3, an upper support surface (ceiling) located above the fixed arm 2 includes arm rails 5 mounted thereon. A slider 6 is slidably mounted and driven on the arm rails 5 by a motor 6A. Below the slider 6 is disposed a reverse L-shaped support arm 7. The support arm 7 includes a horizontal portion 7A which is mounted on the underside of the slider 6 so that the support arm 7 can be rotated about a vertical axis in direction $\theta 1$ by a motor 7C.

The support arm 7 also includes a vertical portion 7B on the inner side of which a connector member 8 is mounted so that it can be rotated about a horizontal axis in direction $\theta 2$ by a motor 8A. The C-shaped fixed arm 2 movably extends through the connecting member 8 in the vertical direction along direction $\theta 3$ and can be driven by a motor 8B through the connecting member 8. The X-ray detector 4 can be moved away from and toward the X-ray generator 3 by a motor 4A.

As shown in FIGS. 1 and 2, the angiographic system 1 also has a bed 9 or support which is disposed between the X-ray source S and a projection plane P. A subject, e.g., a patient PA or a mimic object (phantom) is to be placed on the bed 9. The bed 9 may be of a structure that can be moved in the vertical and/or horizontal directions by a known drive mechanism, for example, by a combination of motor and gear train. Furthermore, the bed 9 may be operated independently of the X-ray detector.

The angiographic system 1 further has an image display means, for example, a monitor (not shown) for displaying the image of the patient PA projected onto the projection plane P.

The angiographic system 1 further has an X-ray shield device.

X-ray shielding disk 20: The X-ray shield device includes X-ray shielding disks or plates 20 to be positioned between the X-ray source S of angiographic system 1 and the bed 9. Each of the X-ray shielding disks 20 is made of an X-ray shieldable material, such as lead or tungsten. The shielding disks 20 are circular in this embodiment, but they may take any suitable shape. Alternatively, each of the X-ray shielding disks 20 may be formed by laminating a plate-shaped member made of a material harder than the aforementioned X-ray shieldable material (e.g., lead) on a plate-shaped member made of said X-ray shieldable material.

Shielding disk drive mechanism 30: The X-ray shield device also includes a shielding disk driving mechanism 30 for moving the shielding disks 20 in a plane parallel to the projection plane P, namely, a plane SMP (a plane in which the shielding disk is moved) perpendicular to a path of X-ray irradiation which extends from the X-ray source S to the projection plane P.

FIGS. 1-4 show the shielding disk drive mechanism 30 which is secured to the fixed arm 2 in a manner to provide a fixed distance between the shielding disk drive mechanism 30 and the X-ray generator 3. However, the shielding disk drive mechanism 30 is not particularly limited to such an arrangement. For example, the shielding disk drive mechanism 30 may be arranged so that it can be supported by any support means independent of the fixed arm 2 and moved between the bed 9 and the X-ray source S in said path of X-ray irradiation. Alternatively, the shielding disk drive mechanism 30 may be stationary if both the X-ray generator 3 and X-ray detector 4 opposed to the X-ray generator 3 are stationary. In such a case, the shielding disk drive mechanism 30 may be fixedly mounted on the underside of the bed, for example. In any case, when the X-ray shield device of the present invention is to be used, the shielding disk drive mechanism 30 should be positioned such that the shielding disk movement plane SMP will be parallel to the projection plane P of the X-ray detector 4.

Figure 5A:
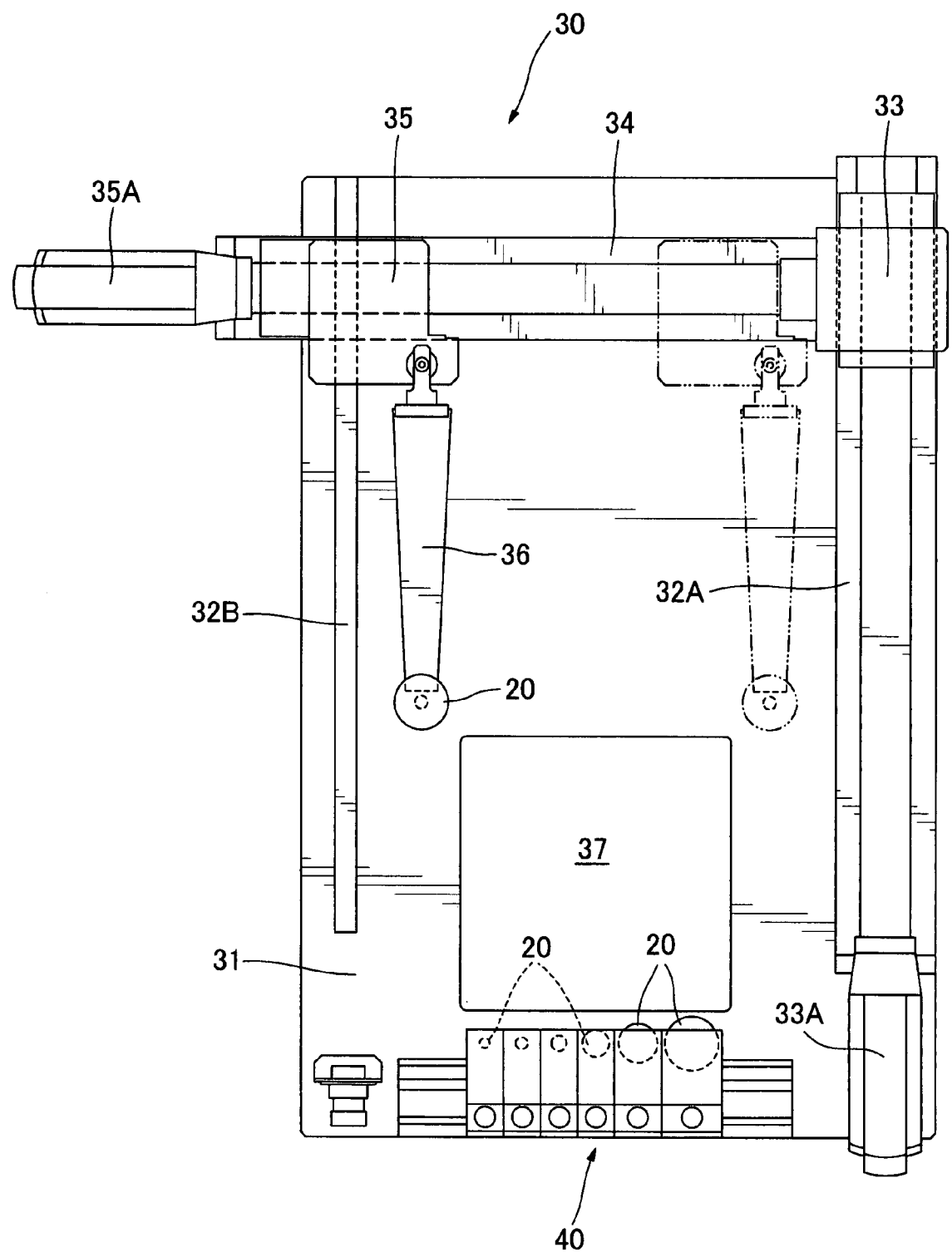
FIG. 5A is a plan view of a shielding disk drive mechanism in the X-ray shield device.

As shown in FIG. 5A, the shielding disk drive mechanism 30 has a flat base frame 31 on which a pair of X-axis guides 32A and 32B are fixedly mounted to extend parallel to each other. A first sliding member 33 is slidably mounted on one of the X-axis guides 32A. The first sliding member 33 is driven by a first stepping motor 33A through a linear ball-and-screw shaft (not shown). A Y-axis guide 34 extends from the first sliding member 33 perpendicular to the X-axis guides 32A and 32B. The Y-axis guide 34 includes a free end portion which is slidably supported by the X-axis guide 32B through a guide roller (not shown) which is mounted on the underside of the Y-axis guide 34.

A second sliding member 35 is slidably mounted on the Y-axis guide 34. The second sliding member 35 is driven by a second stepping motor 35A mounted on the Y-axis guide 34 through a linear ball-and-screw shaft.

The motors 33A and 35A may be servomotors and preferably provided with brakes. A mechanism for driving each of the sliding members 33 and 35 may be any known mechanism such as a combination of a motor with a rack and pinion mechanism or a timing belt mechanism.

A radioparent or X-ray transmission arm 36 extends from the second sliding member 35 parallel to the base frame 31. The arm 36 includes a supporting portion for supporting the X-ray shielding disk 20. The supporting portion of the arm 36 may be of any shape and structure if it can support the X-ray shielding disk 20.

Figure 5B:
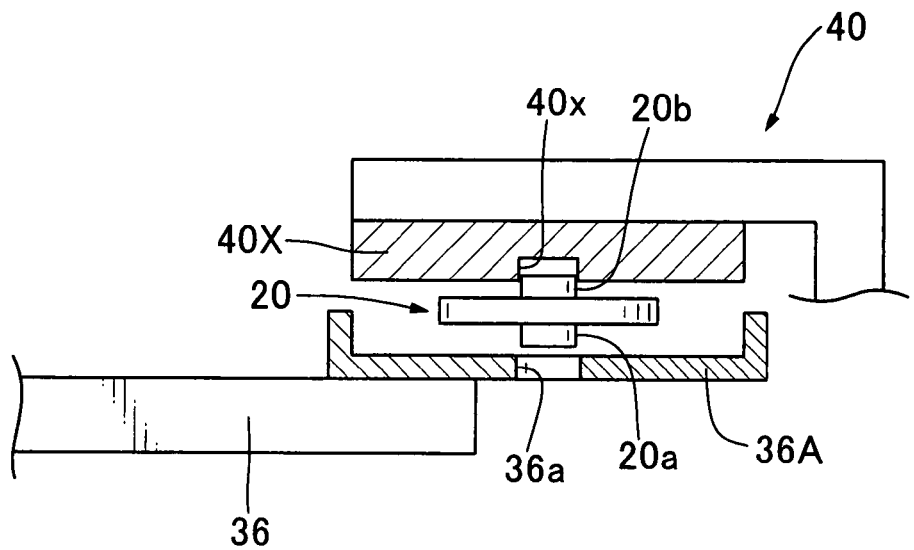
FIG. 5B is a schematic cross-sectional view showing, in a partially enlarged scale, the shielding disk drive mechanism of FIG. 5A with a shielding disk rack.

As can be seen from FIG. 5B, the supporting portion of the arm 36 in this embodiment is formed into a dish-shaped tray 36A including an upwardly extending periphery so that the dish-shaped tray 36A can detachably support X-ray shielding disks 20 having different sizes. The central portion of the tray 36A includes a guide/retention aperture 36a formed therethrough. On the other hand, a protruding pin 20a extends downwardly from the underside of the X-ray shielding disk 20 at the central part thereof. The protruding pin 20a can be inserted into and held by the guide/retention aperture 36a in the supporting portion of the arm 36. Thus, the X-ray shielding disk 20 can be detachably supported by the supporting portion of the arm 36. The X-ray shielding disk 20 also includes a protruding pin 20b extending upwardly from the top of the X-ray shielding disk 20 at the central part thereof.

Each of the first and second stepping motors 33A and 35A includes an encoder which can output the information about the position of the corresponding one of the first and second sliding members 33, 35. Therefore, the position of the X-ray shielding disk 20 in the shielding disk drive mechanism 30 can be always specified. The base frame 31 further includes a through-hole 37 through which X-rays are allowed to pass through.

The aforementioned structure of the shielding disk drive mechanism 30 for moving the X-ray shielding disks 20 in the shielding disk movement plane SMP is per se realized by any one of various known techniques, but not limited to such a structure as described in connection with FIG. 5.

Figure 17:
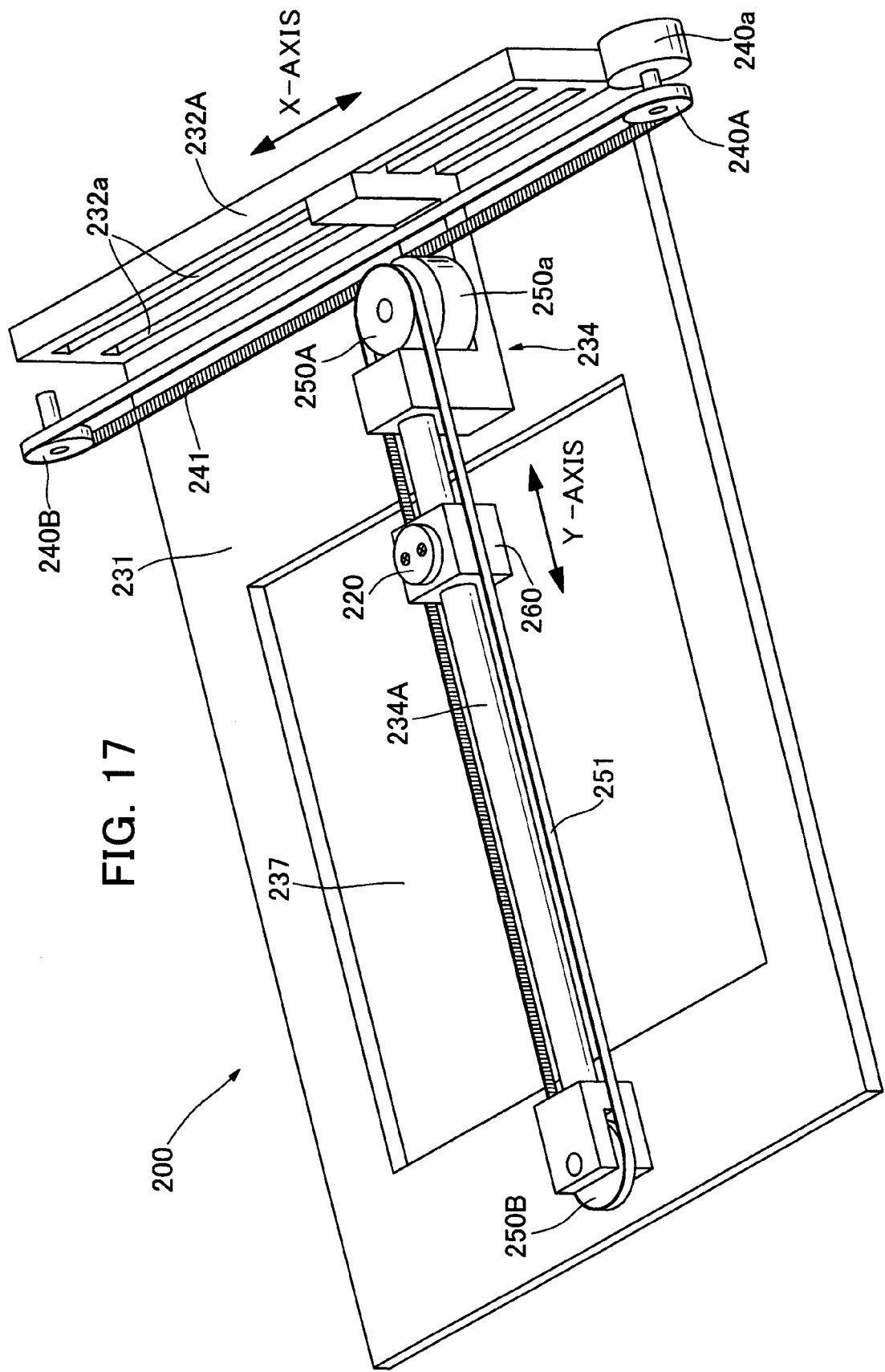
FIG. 17 is a schematic perspective view showing an alternative shielding disk drive mechanism.

For example, the shielding disk drive mechanism 1 may be configured as shown in FIG. 17. This alternative shielding disk drive mechanism generally denoted by a reference numeral 200 includes a base frame 231 having a through-hole 237 through which X-rays pass. The base frame 231 includes an X-axis guide 232A anchored thereto.

The X-axis guide 232A rotatably supports a pair of rollers 240A and 240B spaced apart from each other along the length thereof. One of the rollers 240A is driven by a motor 240a. An endless drive belt 241 is passed around and spanned between the rollers 240A and 240B. The endless drive belt 241 is partially fastened to the respective rollers 240A and 240B.

A Y-axis guide 234 is slidably guided in a guide slot 232a of the X-axis guide 232A along the length thereof and extends perpendicular to the X-axis guide 232A. The Y-axis guide 234 is fastened at one end to the endless drive belt 241. Therefore, when the endless drive belt 241 is driven, the Y-axis guide 234 is slidably driven along the length of the X-axis guide 232A.

The Y-axis guide 232A rotatably supports a pair of rollers 250A and 250B spaced apart from each other along the length thereof. One of the rollers 250A is driven by a motor 250a. An endless drive belt 251 is passed around and spanned between the rollers 250A and 250B. The endless drive belt 241 is partially fastened to the respective rollers 240A and 240B.

The Y-axis guide 234 also has a slide guide 234A which extends therefrom in the longitudinal direction. A shielding disk support member 260 is slidably mounted on the slide guide 234A. The shielding disk support member 260 is anchored to the endless drive belt 251. Therefore, when the endless drive belt 251 is driven, the shielding disk support member 260 is slidably driven along the slide guide 234A. Any one of various X-ray shielding disks 220 having different sizes can be detachably mounted on the shielding disk support member 260 through screws. The endless drive belt 251, slide guide 234A and shielding disk support member 260 are formed of any material of low X-ray shielding property such as plastic.

In this manner, such a shielding disk drive mechanism 200 can also move each of the X-ray shielding disks 20 (220) in the aforementioned shielding disk movement plane SMP.

Figure 6:
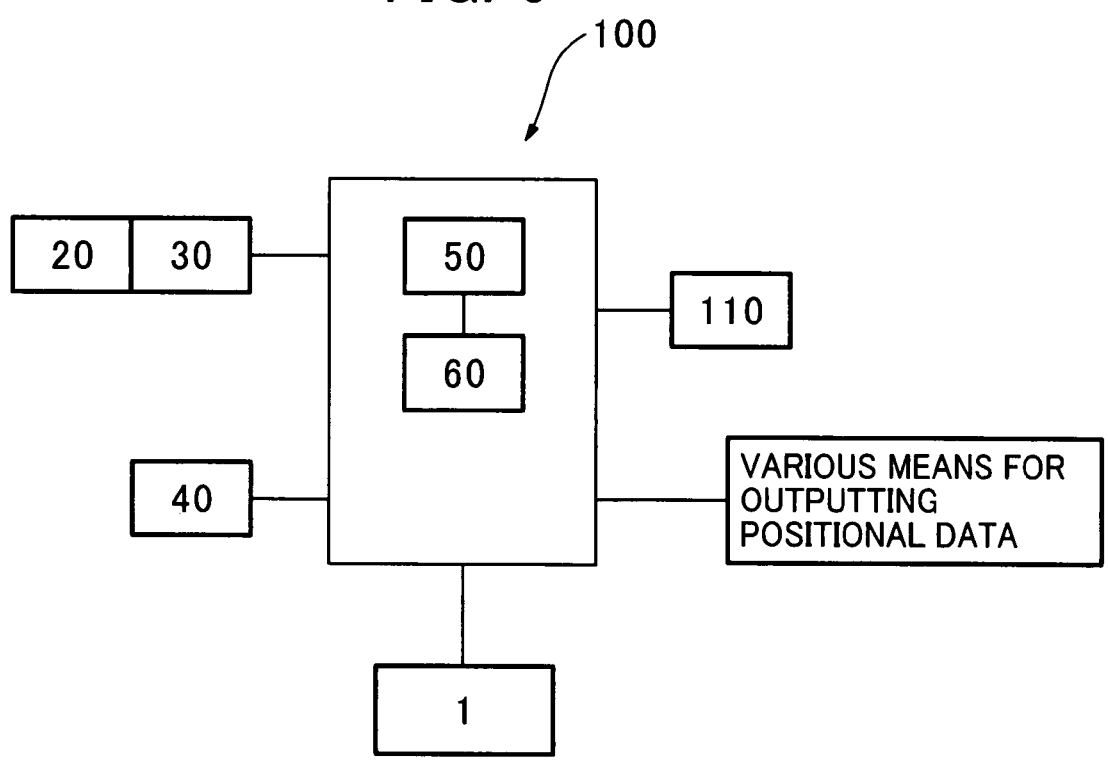
FIG. 6 is a block diagram illustrating the structure of the X-ray shield device.

Control Unit 100: As shown in FIG. 6, the X-ray shield device further includes a control unit 100 for controlling the shielding disk drive mechanism 30. That is to say, various stepping motors used for the shielding disk drive mechanism 30 are controlled by the control unit 100 (in both the embodiments).

The control unit 100 is connected to a command input unit 110 such that all or part of the control executed by the control unit 100 can be manually performed through the command input unit 110.

Means for exchanging one X-ray shielding disk for another: The X-ray shield device further includes a shielding disk exchanging means for exchanging one X-ray shielding disk 20 supported by the supporting portion of the arm 36 for another X-ray shielding disk 20 of different size.

The shielding disk exchanging means has a shielding disk rack 40 mounted on the base frame 31, as shown in FIG. 5A. As shown in FIG. 5B, the shielding disk rack 40 comprises a plurality of electromagnet members 40X which, in this embodiment, releasably holds six X-ray shielding disks 20 having different diameters. Each of the electromagnet members 40X can hold the corresponding one of the X-ray shielding disks 20 when that electromagnet member 40X is energized. When the electromagnet member 40X is de-energized, it can release that X-ray shielding disk 20. Each of the electromagnet members 40X includes a guide/retention aperture 40x formed in the underside thereof. The guide/retention aperture 40x is adapted to guide and retain the protruding pin 20b of the corresponding X-ray shielding disk 20.

Each of the electromagnet members 40X in the shielding disk rack 40 is energized or de-energized according to a command from the control unit 100.

Therefore, when the tray 36A (which does not hold any shielding disk 20 now) of the arm 36 in the shielding disk drive mechanism 30 has been moved below one of the electromagnet members 40X holding an X-ray shielding disk 20 of the desired size and if that electromagnet member 40X is de-energized, the shielding disk 20 is released from the electromagnet member 40X and then received by the tray 36A. Thus, the protruding pin 20a of that shielding disk 20 is guided and held by the guide/retention aperture 36a of the tray 36A. On the other hand, when the tray 36A of the arm 36 holding a shielding disk 20 has been moved below the empty electromagnet member 40X and if the latter is energized, the shielding disk 20 of the tray 36A is electromagnetically attracted by that electromagnet member 40X. The protruding pin 20b of that shielding disk 20 is then guided and held by the guide/retention aperture 40x of the electromagnet member 40X.

The mechanism for holding and releasing the X-ray shielding disks 20 in the shielding disk rack 40 is not limited to the aforementioned arrangement, but may be realized by any suitable known technique.

Figure 7:
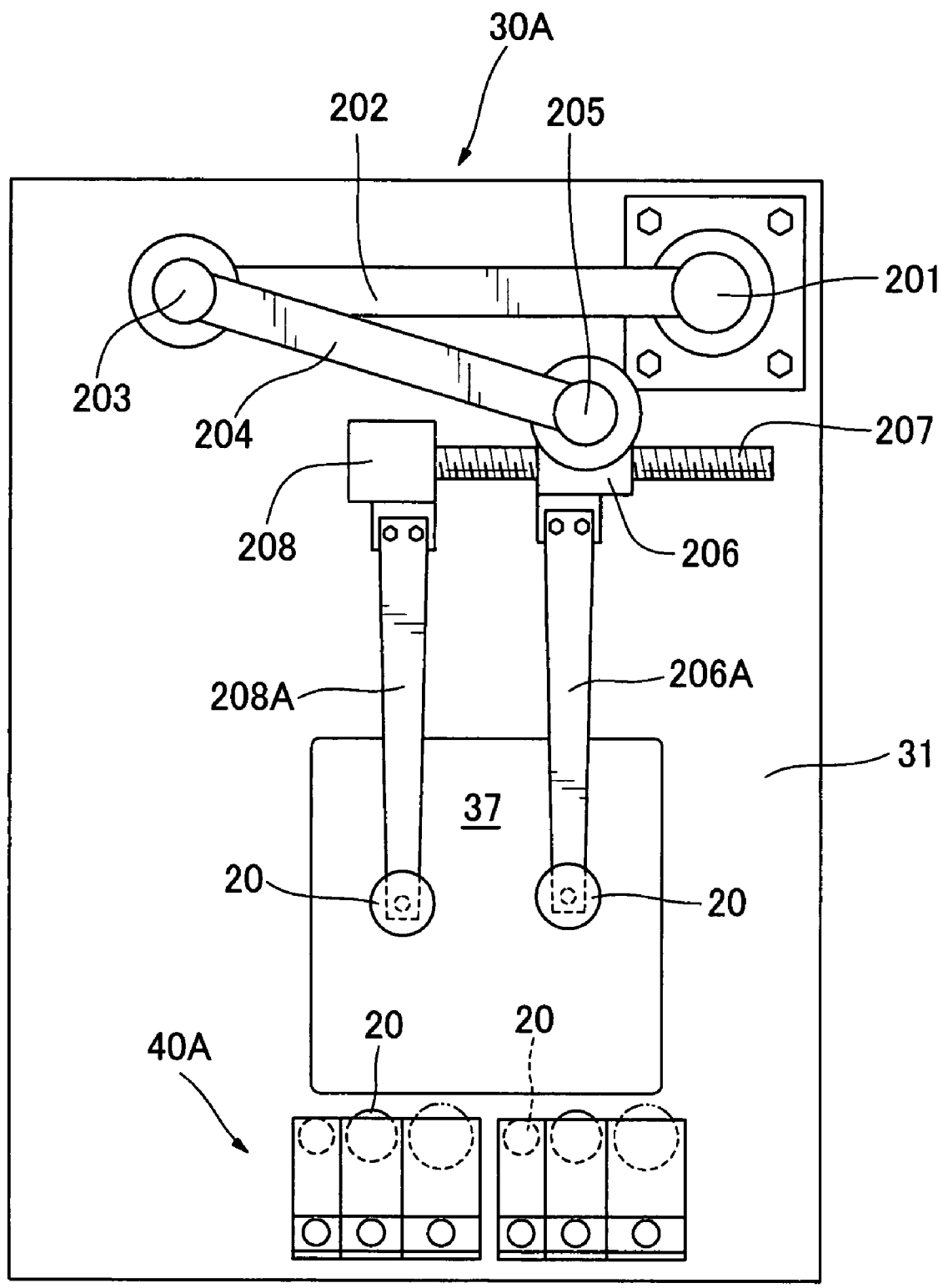
FIG. 7 is a schematic plan view showing an alternative embodiment which comprises a shielding disk drive mechanism and a shielding disk exchanging means.

Alternative form of shielding disk drive mechanism 30 plus shielding disk exchanging means: FIG. 7 shows an alternative form of such shielding disk drive mechanism 30 plus shielding disk exchanging means as shown in the FIG. 5.

Only parts of this alternative form different from those of the shielding disk drive mechanism 30 plus shielding disk exchanging means shown in the FIG. 5 will now be described. Components similar to those of the shielding disk drive mechanism 30 plus shielding disk exchanging means shown in the FIG. 5 will be denoted by similar reference numerals.

Referring to FIG. 7, there is shown a shielding disk drive mechanism 30A which includes a first spindle 201 rotatably mounted on a base frame 31 and a first arm 202 mounted on the first spindle 201. The first spindle 201 can be moved upwardly and downwardly in a direction perpendicular to the base frame 31.

In a further alternative form, the first arm 202 may be moved (up and down) along the first spindle 201. Alternatively, a third spindle 205 which will be described later may be moved vertically relative to the base frame 31. Alternatively, a first support housing 206 which will be described later may be moved (up and down) along the third spindle 205. In brief, it is preferred that arms 206A and 208A which will be described later can be moved up and down relative to the base frame 31.

Referring again to FIG. 7, there is shown a second spindle 203 which is rotatably mounted on the free end portion of the first arm 202 and which extends parallel to the first spindle 201. A second arm 204 is mounted on the second spindle 203. A third spindle 205 is rotatably mounted on the free end portion of the second arm 202 and extends parallel to the first spindle 201. A first support housing 206 is rotatably mounted on the third spindle 205.

A radioparent arm 206A extends from the first support housing 206 parallel to the base frame 31. The free end portion of this arm 206A includes a first supporting portion for supporting the X-ray shielding disk 20.

The first support housing 206 also includes a guide bore (not shown) formed therein and which extends in a direction perpendicular to the arm 206A and parallel to the base frame 31. A linearly slidable arm 207 is slidably disposed within this guide bore. The linearly slidable arm 207 is driven by a stepping motor (not shown) which is received in the first support housing 206.

A second support housing 208 is mounted on the linearly slidable arm 207 at one end. A radioparent arm 208A extends from the second support housing 208 parallel to the arm 206A. The free end portion of the arm 208A includes a second supporting portion for supporting the X-ray shielding disk 20.

In this regard, the first spindle 201, second spindle 203 and third spindle 205 can be rotatably driven by stepping motors (not shown) or similar means. The first spindle 201 is further moved up and down by a combination of a stepping motor (not shown) with a linear ball-and-screw shaft mechanism. Each of these stepping motors comprise an encoder which can output the information about the position (angular position) of the corresponding one of the spindles 201, 203 and 205 and also output the information about the vertical position of the first spindle 201 relative to the base frame 31. In this regard, each of the aforementioned drive motors may be in the form of servomotor and is preferably provided with a brake.

In addition, the position information of said slidable arm 207 can also be provided from a stepping motor (not shown) which is housed within the first support housing 206. Therefore, the shielding disk drive mechanism 30 according to this alternative embodiment can always determine the position of the X-ray shielding disk 20 supported by each of the arms 206A and 208A. The two arms 206A and 208A is to protect both the eyes of a patient. The distance between the two X-ray shielding disks can be regulated by the slidable arm 207 depending on the distance between the eyeballs. On the other hand, if only a single X-ray shielding disk 20 is used as in the shielding disk drive mechanism 30 shown in FIG. 5A, the X-ray emitted from the X-ray source S may be restricted into a reduced area of radiation so that an eyeball not shielded by the X-ray shielding disk 20 will not be irradiated by X-rays.

According to this alternative embodiment, the shielding disk exchanging means also has a shielding disk rack 40A mounted on the base frame 31.

Figure 8:
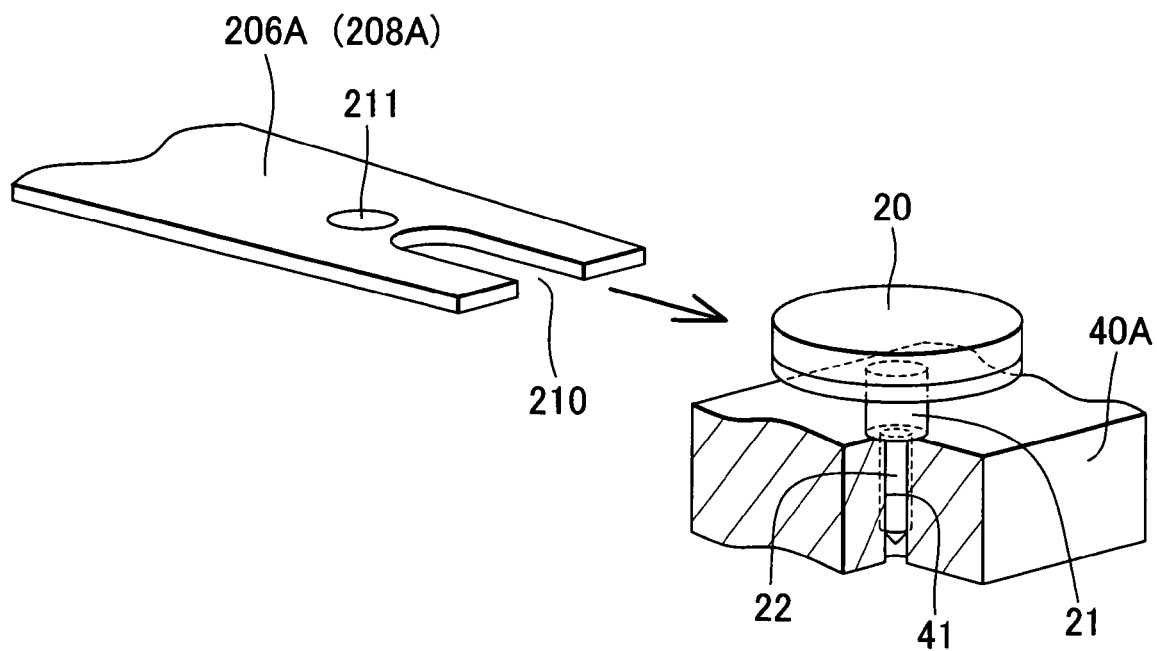
FIG. 8 is a schematic view showing, in a partially enlarged scale, the shielding disk drive mechanisms of FIG. 7.
Figure 9A:
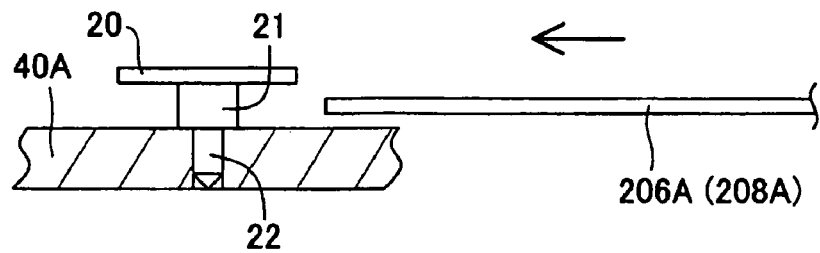
FIGS. 9A-9E are views illustrating a manner in which an X-ray shielding disk in the shielding disk rack is picked up and held by the shielding disk drive mechanism.
Figure 9B:
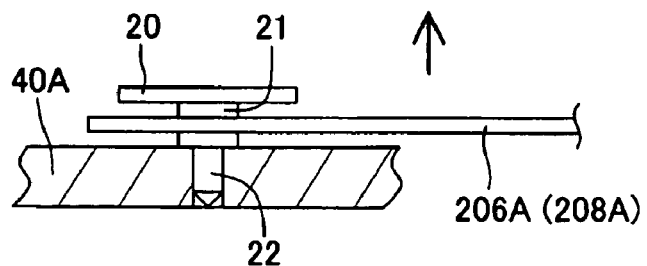
Figure 9C:
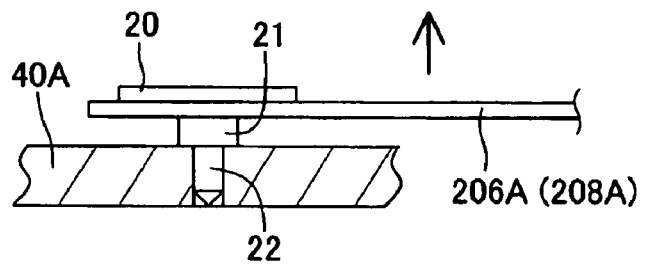
Figure 9D:
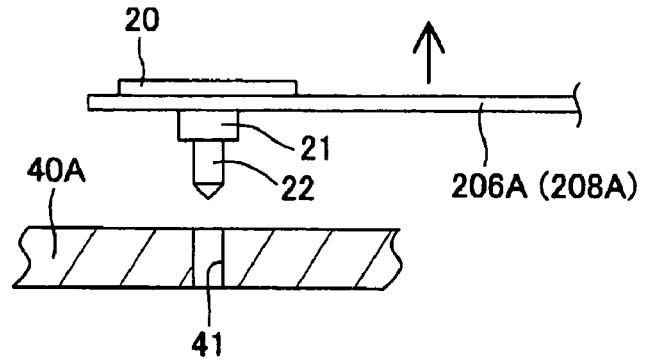
Figure 9E:
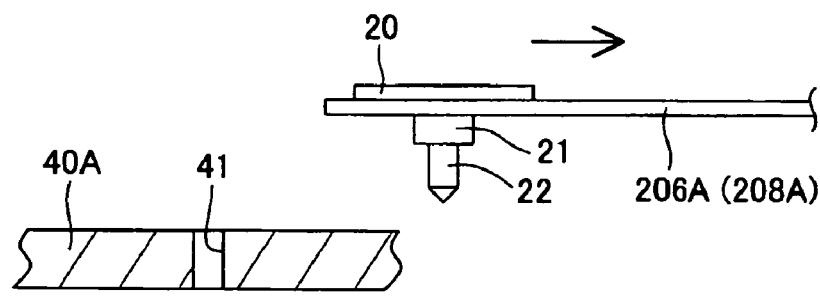
Figures 1, 9:
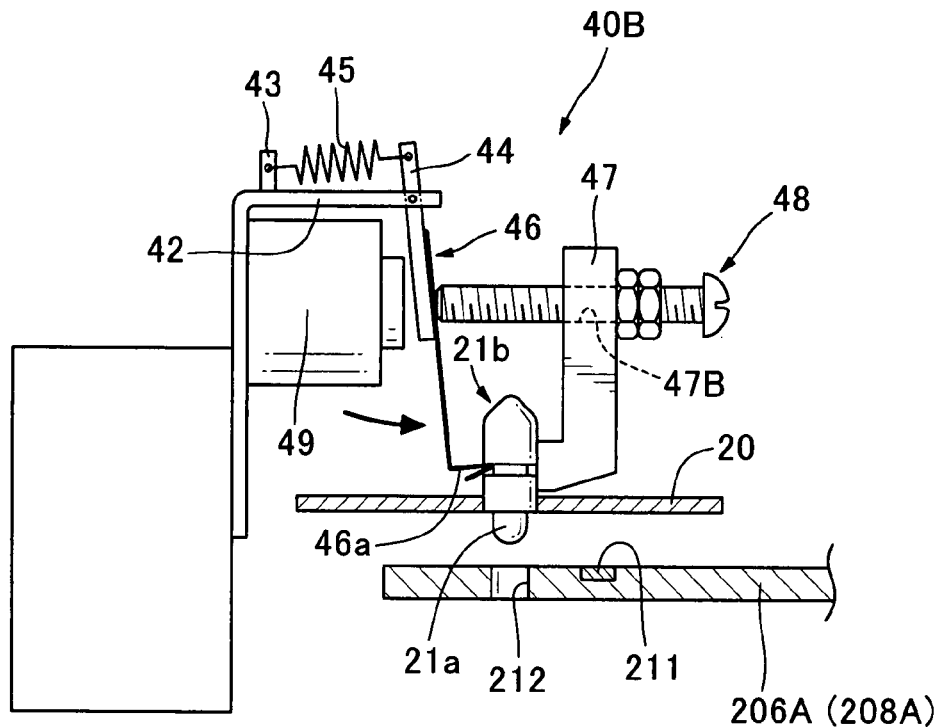
Figures 2, 9:
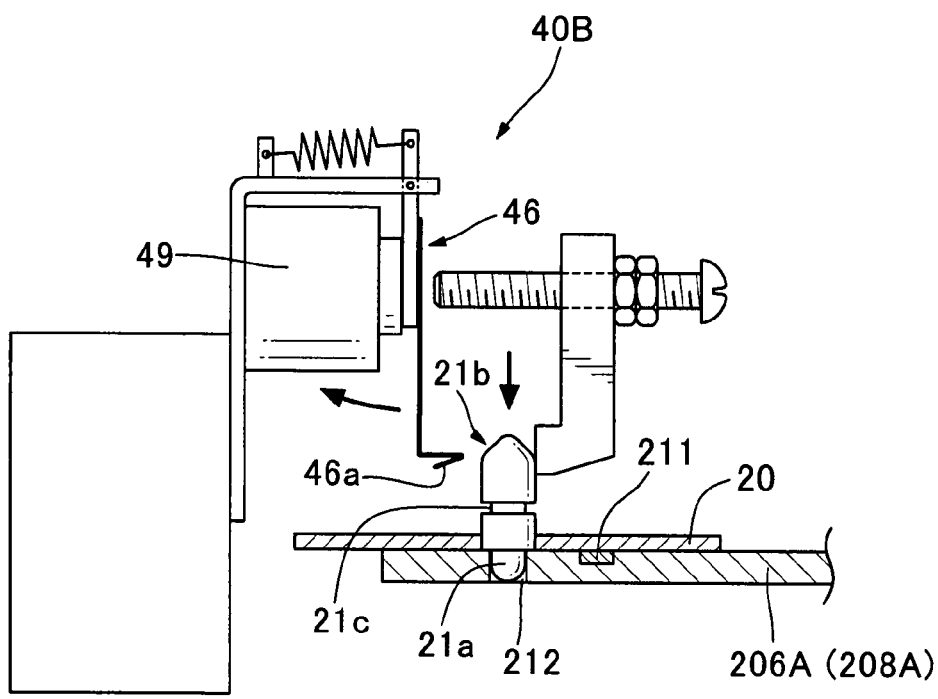
Figures 3, 9:
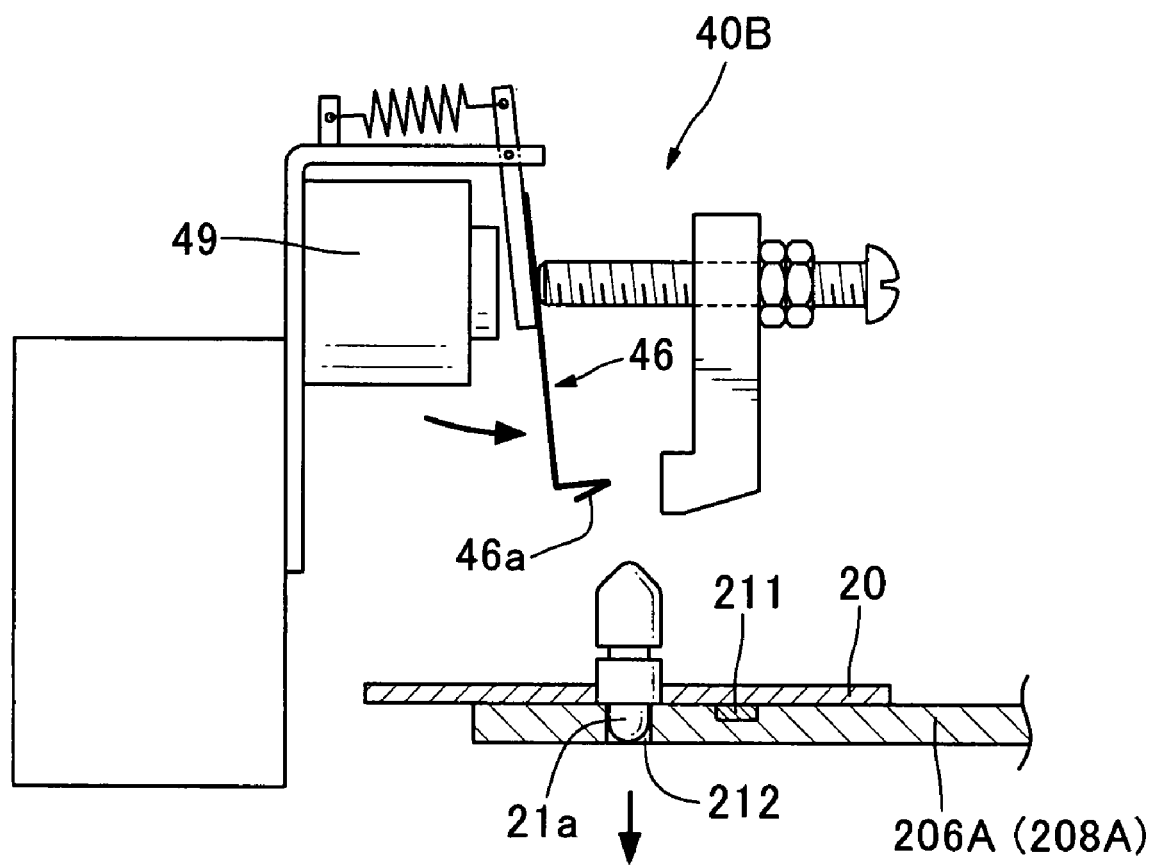

As seen best from FIGS. 7-9, the shielding disk rack 40A releasably holds two sets of X-ray shielding disks 20 (three in each set according to this embodiment) having different sizes.

The shielding disk rack 40A comprises holding bars 40a for releasably holding several X-ray shielding disks 20. Each of the holding bars 40a includes three holding recesses 41 formed therein and extending perpendicular to the base frame 31.

According to this alternative embodiment, each of the X-ray shielding disks 20 comprises a first reduced diameter portion 21 extending downwardly from the underside thereof at the center and a second reduced diameter portion 22 extending downwardly from the bottom end of the first reduced diameter portion 21 at the center, the second reduced diameter portion 22 having its diameter smaller than that of the first reduced diameter portion 21. The diameter of the second reduced diameter portion 22 is slightly smaller than that of the holding recess 41 in the shielding disk rack 40A while the diameter of the first reduced diameter portion 21 is larger than that of the holding recess 41 in the shielding disk rack 40A.

The first reduced diameter portion 21 is formed of magnetic material. Thus, the first reduced diameter portion 21 is magnetically attracted by the corresponding holding bar 40a when the second reduced diameter portion 22 is inserted into the corresponding holding recess 41 of the holding bar 40a so that the bottom face of the first reduced diameter portion 21 is engaged by the holding bar 40a. Thus, when the fixed arm 2 is rotated from such a position as shown in FIGS. 1-3 so that the shielding disk drive mechanism 30 and thus the shielding disk rack 40A is inverted, the X-ray shielding disk 20 can be prevented from falling out of the shielding disk rack 40A. The second reduced diameter portion 22 may be formed of magnetic material rather than the first reduced diameter portion 21.

As can be seen best from FIG. 8, the free end (i.e., the first or second supporting portion) of each of the arms 206A and 208A in the shielding disk drive mechanism 30A includes a U-shaped or semi-oval cutout portion 210 and a magnet 211 located adjacent to the cutout portion 210. The width of the U-shaped cutout portion 210 is slightly larger than the first reduced diameter portion 21 of the X-ray shielding disk 20.

In conjunction with the magnet 211, the underside of each of the X-ray shielding disks 20 to be used is formed of any suitable material that can be magnetically attracted by the magnet 211.

If both the arms 206A and 208A of the shielding disk drive mechanism 30A hold no X-ray shielding disk 20, each of the arms 206A and 208A can receive an X-ray shielding disk 20 of the desired size from the corresponding holding bar 40a by first regulating the spacing between the two arms 206A and 208A into the spacing between the corresponding set of X-ray shielding disks 20 in the shielding disk rack 40A, thereafter moving the free ends of the arms 206A and 208A to approach the respective X-ray shielding disks 20 held by the shielding disk rack 40A as shown in FIG. 9(A), and finally positioning the first reduced diameter portions 21 of the X-ray shielding disks 20 in the respective U-shaped cutout portions 210 as shown in FIG. 9(B).

Then, the first spindle 201 is moved upwardly from the standard plane in the base frame 31 so that the arms 206A and 208A are caused to be engaged by the undersides of the corresponding X-ray shielding disks 20 as shown in FIG. 9(C). Thus, the magnets 211 of the arms 206A and 208A magnetically attract the undersides of the X-ray shielding disks 20 into engagement therewith. Subsequently, the first spindle 201 is further moved upwardly from the base frame 31 against the magnetic force acting between the holding bars 40a and the first reduced diameter portions 21. Thus, the second reduced diameter portions 22 of the X-ray shielding disks 20 are pulled out from the holding recesses 41 of the shielding disk rack 40A as shown in FIG. 9(D).

The arms 206A and 208A that have received the X-ray shielding disks 20 are then moved away from the shielding disk rack 40A. Thereafter, the first spindle 201 is moved downwardly to the standard plane so that the X-ray shielding disks 20 are positioned in a shielding disk movement plane SMP as will be described.

In order to cause the X-ray shielding disks 20 on the arms 206A and 208A to be held by the shielding disk rack 40A, the aforementioned operation may be reversed.

FIGS. 9-1 to 9-3 show an alternative embodiment of the shielding disk exchanging means shown in FIGS. 8 and 9.

According to this alternative embodiment, the free end portion of each of the arms 206A and 208A in the shielding disk drive mechanism 30A includes a guide/hold aperture 212 formed therethrough, in place of the cutout portions 210 shown in FIGS. 8 and 9.

On the other hand, each of the X-ray shielding disks 20 to be used includes a protruding pin 21a extending downwardly from the underside thereof at the center. The protruding pin 21a is so dimensioned and shaped so that it can be guided and held by the corresponding one of guide/hold apertures 212. Each of the X-ray shielding disks 20 also includes a protruding pin 21b extending upwardly from the top thereof at the center. The protruding pin 21b includes a circumferential groove 21c formed therein. According to this alternative embodiment, the shielding disk rack 40A of FIGS. 8 and 9 is replaced by a shielding disk rack 40B.

The shielding disk rack 40B comprises a horizontal fixed plate 42, a protruding wall 43 extending upwardly from one end of the horizontal fixed plate 42 and a pivot plate 44 pivotably mounted in a bifurcated portion (not shown) which is cut out at the other end of the horizontal fixed plate 42. A spring 45 is operatively mounted between the protruding wall 43 and the top end of the pivot plate 44. The spring 45 acts such that the pivot plate 44 is rotated counter-clockwise as viewed in FIG. 9-1.

A shielding disk moving/holding member 46 is mounted on the lower part of the pivot plate 44 which is located below the horizontal fixed plate 42. The shielding disk moving/holding member 46 extends downwardly from the pivot plate 44, the bottom free end portion 46a thereof being bent to extend into the circumferential groove 21 of the protruding pin 21b in the X-ray shielding disk 20. A shielding disk fixing/holding member 47 is located opposed to the shielding disk moving/holding member 46. A shielding disk 20 is held in the shielding disk rack 40B when the bottom free end 46a of the shielding disk moving/holding member 46 extending into the circumferential groove 21c of the protruding pin 21b of the shielding disk 20 presses the protruding pin 21b against the shielding disk fixing/holding member 47.

The shielding disk fixing/holding member 47 includes a threaded hole 47B formed therein. A screw stopper 48 threadedly engages in the threaded hole 47B. The screw stopper 48 functions to prevent the pivot plate 44 from being rotated beyond a predetermined position.

An electromagnet 49 is located below the horizontal fixed plate 42 and adjacent to the lower part of the pivot plate 44. When this electromagnet 49 is energized, it can magnetically attract the lower part of the pivot plate 44 into engagement therewith against the biasing force of the spring 45.

According to this alternative embodiment, each of the arms 206A and 208A receives an X-ray shielding disk 20 of the desired size from the shielding disk rack 40B by moving the free ends of the arm 206A or 208A by the shielding disk drive mechanism 30A so that the guide/hold aperture 212 thereof is positioned below the lower part of the corresponding protruding pins 21a in that X-ray shielding disk 20 held by the shielding disk rack 40B, as shown in FIG. 9-1.

Subsequently, the electromagnet 49 is energized. Then, the corresponding pivot plate 44 is rotated clockwise against the biasing force of the spring 45, as shown in FIG. 9-2. As a result, the free and bottom end 46a of the corresponding shielding disk moving/holding member 46 is separated from the circumferential groove 21c of the protruding pin 21b in the X-ray shielding disk 20. Then, the X-ray shielding disk 20 falls freely. The protruding pin 21a of the X-ray shielding disk 20 is guided and held by the guide/hold aperture 212 of each of the arms 206A and 208A while at the same time the X-ray shielding disk 20 is magnetically attracted by each of the arms 206A and 208A.

When the first spindle 201 is subsequently moved downwardly from the standard plane, each of the arms 206A and 208A is moved downwardly away from the shielding disk rack 40B, as shown in FIG. 9-3. Thereafter, the first spindle 201 is moved upwardly to the standard plane so that the X-ray shielding disk 20 is located in a shielding disk movement plane SMP described below. Before or after this time, the electromagnet 49 is de-energized. Thus, the free and bottom end portion 46a of the corresponding shielding disk moving/holding member 46 is returned back to the same position as is shown in FIG. 9-1.

In order to cause the shielding disk rack 40B to hold the X-ray shielding disks 20 held by the arms 206A and 208A, the aforementioned operation may be reversed.

Shielding position determining means: The X-ray shield device also has a shielding position determining means for computing or determining a "shielding position SH" which is a position at which each shielding disk 20 should be centered and at which a line C extending through the X-ray source S and the center of a particular location on a patient PA at which the irradiation of the X-ray from the X-ray source S should be blocked, intersects a plane in which the shielding disk is moved by means of the shielding disk drive mechanism 30.

For convenience sake, the following description will be made assuming that a particular location on the patient PA at which the irradiation of the X-ray from the X-ray source S should be blocked is an eyeball EB.

Figure 10:
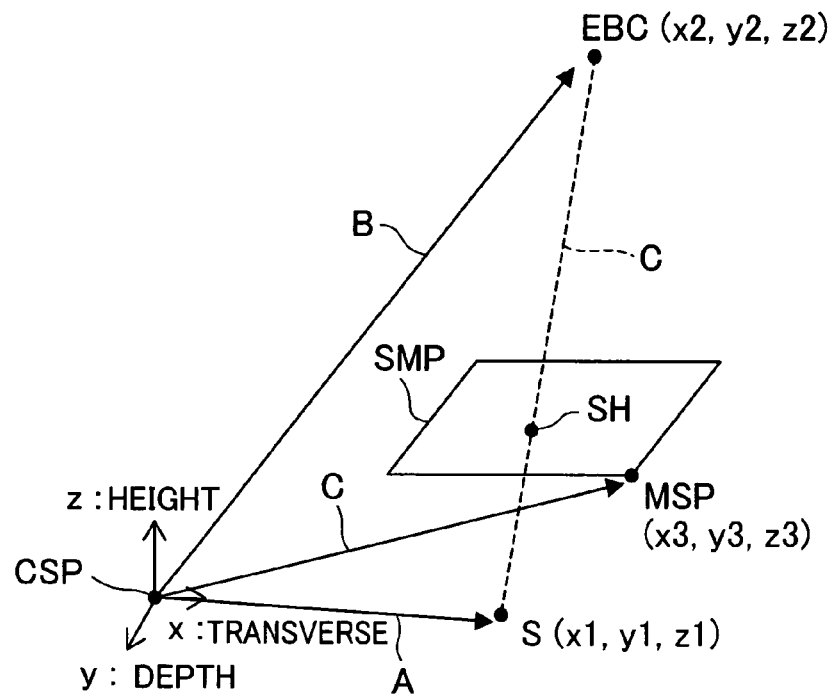
FIG. 10 is a schematic view illustrating the positional relationship between a common reference point, an X-ray source S, a shielding position SH and an eyeball position EBC.

The shielding position determining means comprises an X-ray source position measuring device for measuring the position of the X-ray source S relative to a common reference point CSP shown in FIG. 10, a shielding disk driver position measuring device for measuring the position of the shielding disk drive mechanism 30 relative to the common reference point CSP, an eyeball position measuring device for measuring the position of an eyeball EB relative to the common reference point CSP, and a computing unit 60 for computing or determining the shielding position SH based on data from the X-ray source position measuring device, data from the shielding disk drive mechanism position measuring device and data from the eyeball position measuring device. The term "common reference point CSP" used herein may refer to any suitable point (position) such as a point on a floor on which the angiographic system 1 and X-ray shield device are placed. In this regard, arrows A, B and C in FIG. 10 indicate position vectors determined based on the common reference point CSP.

X-ray source position measuring device: The X-ray source position measuring device may be configured by such means as exemplified below:

(1) Position output means of the angiographic system 1: If each of the aforementioned motors 6A, 7C, 8A and 8B in the angiographic system 1 is provided with a position output means such as an encoder which can output the positional data of the corresponding movable part moved by the corresponding one of these motors in the angiographic system 1, the X-ray source position measuring device can be configured by such position output means and a computing unit 60 for computing or determining the position of the X-ray source S relative to the common reference point CSP based on position output data from that position output means.

(2) Position measuring device to be retrofitted: If each of the motors 6A, 7C, 8A and 8B of the angiographic system 1 is not provided with position output means such as an encoder which can output the position data of the corresponding movable part moved by that motor in the angiographic system 1, the X-ray source position measuring device may be configured by a retrofit position measuring device for measuring the position of the movable part in the angiographic system 1 such as a linear encoder or inclination sensor retrofitted to that movable part and a computing unit 60 for computing or determining the position of the X-ray source S relative to the common reference point based on the position data from the retrofitted position determining device.

In any case, the computing unit 60 may be provided in the control unit 100 as shown in FIG. 6 or externally connected to the control unit 100.

Shielding disk driver position measuring device: The shielding disk driver position measuring device may be configured by the components as exemplified in the following:

(1) Storage unit: If the shielding disk drive mechanism 30 is positioned at a certain position, the shielding disk driver position measuring device may comprise a storage unit 50 for storing position data provided by having previously measured any position of the shielding disk drive mechanism 30 relative to the common reference point CSP, in this embodiment, any particular standard position MSP in the shielding disk movement plane SMP, which position will be referred to "in-movement-plane standard position MSP".

(2) X-ray source position data: If the shielding disk drive mechanism 30 is mounted on the X-ray generator 3 at a predetermined relative position (or a previously measured positional relationship) relative to the X-ray source S the position of which can be measured as described above, the shielding disk driver position measuring device may also comprise the X-ray source S, a storage unit 50 for storing any relative position data between any position of the shielding disk drive mechanism 30 and the in-movement-plane standard position MSP (as in this embodiment), and the aforementioned X-ray source position measuring device.

(3) Bed position data: If the shielding disk drive mechanism 30 is mounted on a bed 9 at a predetermined relative position (or a previously measured positional relationship) relative to the bed 9 the position of which can be measured as described above, the shielding disk driver position measuring device may further comprise the bed 9, a storage unit 50 for storing relative position data between any position of the shielding disk drive mechanism 30 and the in-movement-plane standard position MSP (as in this embodiment), and means for measuring the position of the bed 9.

Figure 18:
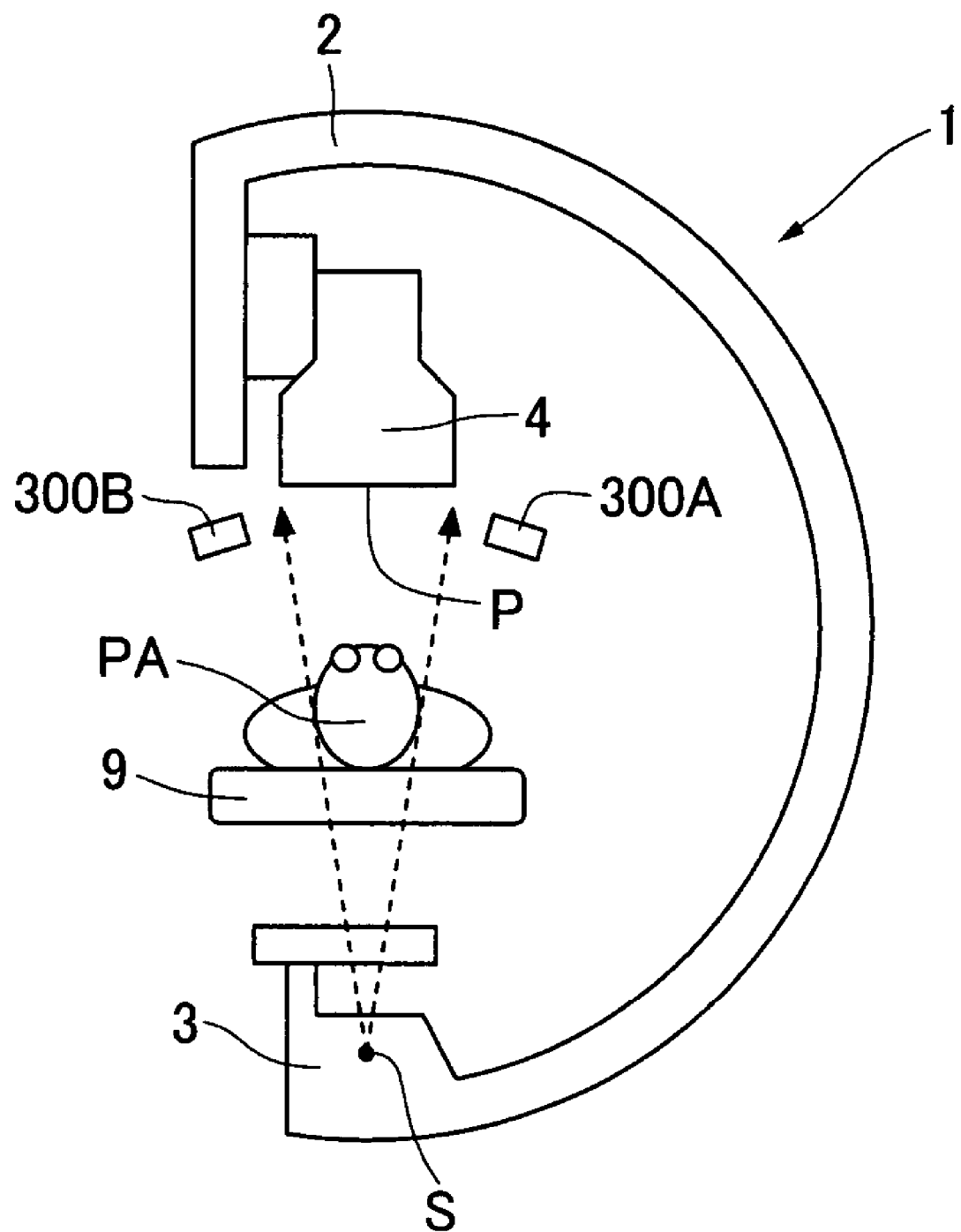
FIG. 18 is a schematic front view partially showing an alternative angiographic system.

(4) Three-dimensional image measuring device based on video cameras: The shielding disk driver position measuring device may still further comprise reflective measurement markers (not shown) mounted on the shielding disk drive mechanism 30 and used for measuring previously the standard position (posture) of the shielding disk drive mechanism 30, a lighting apparatus (not shown) for illuminating the markers, a camera system having two video cameras 300A and 300B (FIG. 18) for imaging the markers, and a computing unit 60 for computing or determining the position/posture of the shielding disk drive mechanism 30 based on the image data of the imaged markers. Such a three-dimensional image measuring arrangement based on video cameras may be in the form of any known position measuring system incorporated into a general motion capturing device, and the detailed structure and operation thereof will not be described further in detail herein.

In either of the aforementioned four cases, the storage unit 50 and computing unit 60 may be provided in the control unit 100 as shown in FIG. 6 or externally connected to the control unit 100.

Eyeball position measuring device: The eyeball position measuring device may be configured by the components as exemplified in the following:

(1) Laser pointer: The eyeball position measuring device may comprise a laser pointer for positioning an eyeball EB at the previously measured or predetermined position relative to the common reference point CSP, and a storage unit 50 for storing the position data of this predetermined position. The storage unit 50 may be provided in the control unit 100 as shown in FIG. 6 or externally connected to the control unit 100.

Such a laser pointer may be in the form of a well-known imaging/positioning laser pointer which has been used for diagnosis by means of an X-ray computed tomography system, and the structure and operation thereof will not be described herein. Alternatively, the eyeball position measuring device may be configured by a well-known imaging/positioning laser pointer with measuring function which has been used for diagnosis in an X-ray computed tomography system. Such a laser pointer is also a well-known device which has been used for diagnosis in an X-ray computed tomography system. By using such a device, the position of an eyeball EB relative to the common reference point CSP can be measured.

(2) Bed position data: If the bed 9 is of power driven type comprising an encoder or the like which can output the position data of the bed 9, the eyeball position measuring device may also comprise the encoder or the like, and a computing unit 60 for computing or determining the position of an eyeball relative to the common reference point CSP based on the position data of the bed from said encoder or the like and also the previously measured distance between the back of the head of a patient PA supported on the bed 9 and the eyeball.

If an even movable bed 9 does not comprise means for outputting the position data of the bad 9, the eyeball position measuring device can comprise a retrofitted bed position measuring device comprising a linear encoder, an inclination sensor or the like which is retrofitted on the bed 9 for measuring the position of the bed 9, and a computing unit 60 for computing or determining the position of an eyeball relative to the common reference point CSP based on the bed position data from the retrofitted bed position measuring device and also the previously measured distance between the back of the head of a patient PA supported on the bed 9 and the eyeball.

In any case, the computing unit 60 may be provided in the control unit 100 as shown in FIG. 6 or externally connected to the control unit 100.

Figure 11:
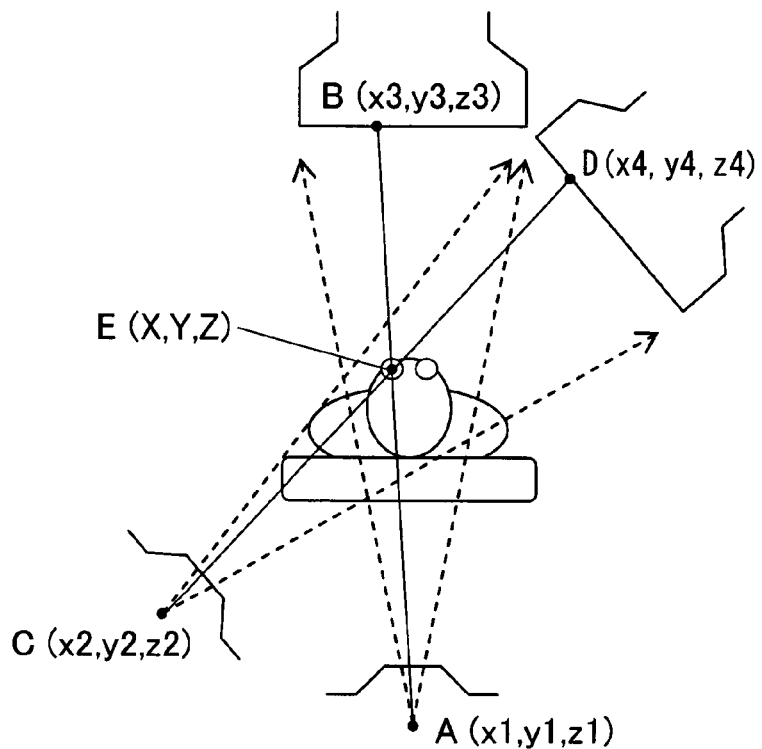
FIG. 11 is a schematic view showing an eyeball position measuring device to which an angiographic system is applied.

(3) Angiographic system: The eyeball position measuring device may further comprise an X-ray fluoroscopic apparatus used as the angiographic system 1, and a computing unit 60 for computing the position of the eyeball relative to the common reference point CSP based on data provided by using the X-ray fluoroscopic apparatus to image the head of a patient PA in two different directions while changing the rotation angle of the arm 2 on which the X-ray generator 3 and X-ray detector 4 are mounted, as shown in FIG. 11 so as to determine the positions of pixels at a location at which an eyeball EB is imaged on each of the visualized images, and to determine coordinates of points B and D on the X-ray detector 4 on which the eyeball EB is imaged, from the actual size of each pixel and the coordinates of the center of the X-ray detector 4. This computing unit 60 may also be provided in the control unit 100 or externally connected to the control unit 100.

As shown in FIG. 11, the computing unit 60 computes the coordinates (X, Y, Z) of an intersection E at which the eyeball is positioned, by use of the following equations (1) and (2) as to the straight lines AB and CD, respectively, based on the coordinates of the points B and D determined by the angiographic system 1.

$$X=x1+s(x3-x1),\ Y=y1+s(y3-y1),\ Z=z1+s(z3-z1) \quad (1)$$

$$X=x2+t(x4-x2),\ Y=y2+1t(y4-y2),\ Z=z2+t(z4-z2) \quad (2)$$

That is to say, the coordinates of the intersection E are determined by substituting constants for x, y and z in the equations to solve them for "s" and "t". If the aforementioned operation is performed to each of the eyeballs, the coordinates (X, Y, Z) of the intersection E at which each eyeball is located can be determined.

(4) Three-dimensional image measuring device based on a video camera: The eyeball position measuring device may further comprise reflective measurement markers (not shown) located near each of the eyeballs, a lighting apparatus (not shown) for illuminating the markers, a camera system having two video cameras 300A and 300B (FIG. 18) for imaging the markers, and a computing unit 60 for computing or determining the position of each eyeball based on the image data of the imaged markers. Such a three-dimensional image measuring arrangement based on video cameras may be in the form of any known position measuring system incorporated into any general motion capturing device, and the structure and operation thereof will not be described further in detail herein.

Computing unit: According to this embodiment, the computing unit 60 is adapted to compute or determine an intersection point between the shielding disk movement plane in which the shielding disk 20 is moved and a central line C extending through the X-ray source S and the center EBC of an eyeball EB, namely, a shielding position SH, based on the data from the X-ray source position measuring device, the data from the eyeball position measuring device and the data from the shielding disk driver position measuring device.

According to this embodiment, the computing unit 60 determines the central line extending through the X-ray source S and the center EBC of an eyeball EB by use of the following equation (3) where the position of the X-ray source S is in a point (x1, y1, z1) and the position EBC of an eyeball is in a point (x2, y2, z2).

$$x=x1+s(x2-x1),\ y=y1+s(y2-y1),\ z=z1+s(z2-z1) \quad (3)$$

On the other hand, the computing unit 60 determines the shielding disk movement plane by use of the following equation (4):

$$a(x-x3)+b(y-y3)+c(z-z3)=0 \quad (4)$$

where the position of the shielding disk drive mechanism (or the in-movement-plane standard position as in this embodiment) is in a point (x3, y3, z3), since the normal vector (a, b, c) of the shielding disk movement plane can be calculated by the shielding disk movement plane being parallel to the projection plane P.

By substituting the equation (3) for the equation (4) to solve for "s," the coordinates of the intersection point (i.e., the shielding position SH) can be determined.

The control unit 100 controls the shielding disk drive mechanism 30 so that a shielding disk 20 (or the center thereof) will be moved to be centered on the shielding position SH determined by the computing unit 60. As described, the position of the shielding disk 20 (or the center thereof) in the shielding disk drive mechanism 30 is determined by the computing unit 60 based on the positional information of the first and second sliding members 33, 35 provided by the first and second stepping motors 33A, 35A. The control unit 100 controls the shielding disk drive mechanism 30 according to the position data of this shielding disk 20 (or the center thereof).

Shielding disk size determining means: The X-ray shield device also comprises a shielding disk size determining means for computing or determining the size (e.g., diameter) of a circular shielding disk 20 suitable for a particular part of a patient PA at which the irradiation of X-ray from the X-ray source S should be blocked, that is, an eyeball in case of the intravascular procedure to be performed against the head of the patient PA.

In the present application, the size of the circular shielding disk 20 suitable for the particular part of the patient PA at which the X-ray irradiation from the X-ray source S should be blocked is understood to refer to one that can block the X-ray from the X-ray generator to any desired part of a human body at which the X-ray irradiation should be avoided while permitting the X-ray irradiation to be irradiated to another part of the human body which needs the X-ray irradiation from the X-ray generator.

For convenience sake, the following description will similarly be made assuming that the particular part of the patient PA at which the X-ray irradiation from the X-ray source S should be blocked is one of eyeballs EB of the patient.

The shielding disk size determining means comprises the above described shielding position determining means, an eyeball size storing device for storing data relating to the size of an eyeball projected onto a plane EBP perpendicular to the center line C which passes through the X-ray source S and the center of the eyeball EB, and a computing unit 60 for computing or determining the diameter of a shielding disk 20 suitable for the eyeball EB based on data provided from the shielding position determining means and eyeball size storing device.

Eyeball size storing device: The eyeball size storing device may be configured by a storage unit for storing any numerical data (e.g., 24 mm for adult) such as numerical data commonly indicative of an anatomically ocular diameter or numerical data that is an average ocular diameter as the size of an eyeball EB projected onto the plane EBP perpendicular to the center line C which extends through the X-ray source S and the center of the eye ball EB.

Computing unit: The computing unit 60 computes or determines the diameter (d) of a shielding disk 20 suitable for each eyeball to be shielded, based on the data from the aforementioned shielding position determining means and eyeball size storing device.

Figure 12:
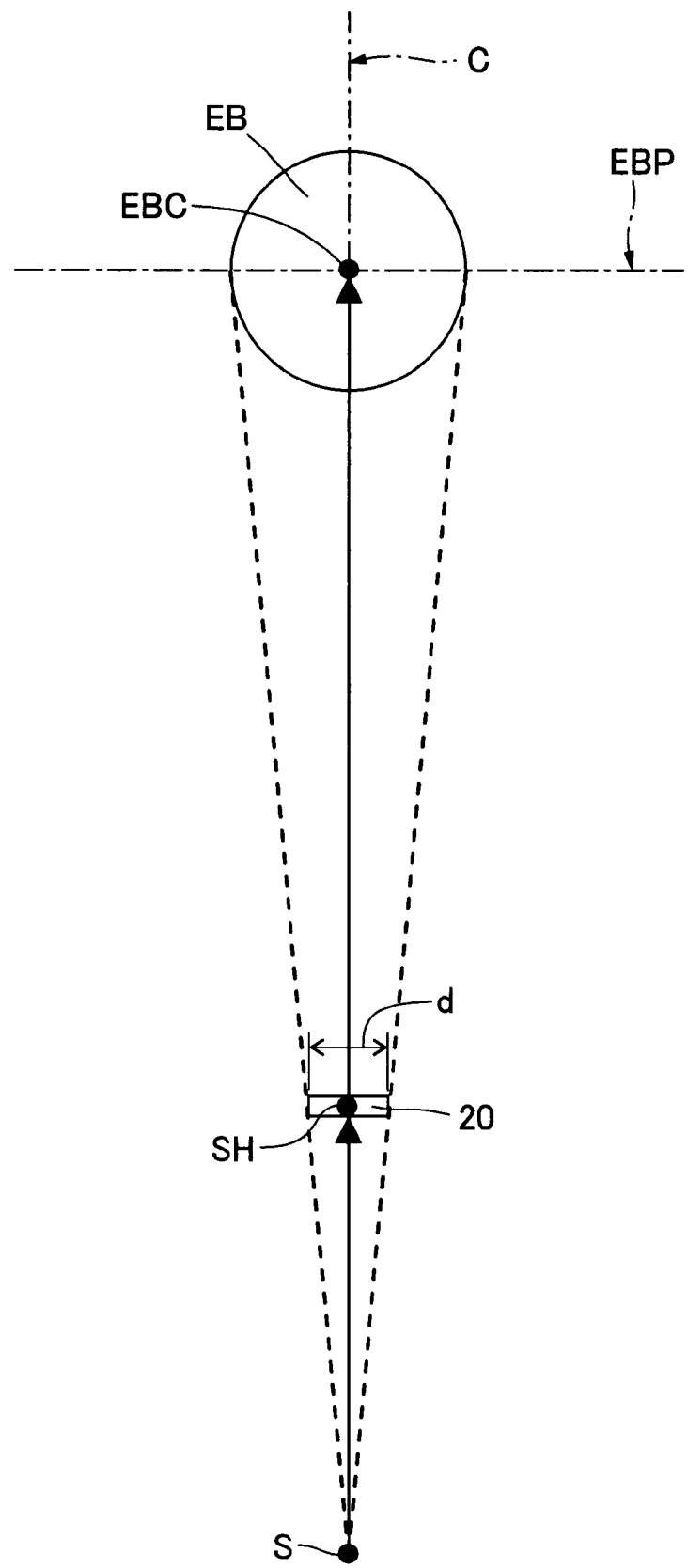
FIG. 12 is a schematic view illustrating the positional relationship between the X-ray source of the angiographic system, a shielding disk of the X-ray shield device and an eyeball which should be shielded against X-rays.

For better understanding of the present invention, FIG. 12 schematically illustrates the relationship between the X-ray source position S, the eyeball position EBC and the shielding position SH.

In accordance with this embodiment, the computing unit 60 uses the following equation (5) to determine the diameter (d) of a shielding disk 20.

$$d = \text{(Distance between the X-ray source position } S \text{ and the shielding position } SH)/(\text{Distance between the X-ray source place } S \text{ and each eyeball position } EBC) \times \text{the diameter of an eyeball} \quad (5)$$

In other words, the diameter (d) of the corresponding shielding disk 20 can be determined according to the following equation 6):

$$d = \sqrt{\{(x2-x1)^2 + (y2-y1)^2 + (z2-z1)^2\}} / \sqrt{\{(x3-x1)^2 + (y3-y1)^2 + (z3-z1)^2\}} \times \text{the diameter of an eyeball} \quad (6)$$

where the X-ray source position S is at (x1, y1, z1), the shielding position SH is at (x2, y2, z2) and the eyeball position EBC is at (x3, y3, z3).

Operation of X-ray shield device: Operation of the aforementioned X-ray shield device will be described below.

When the X-ray shield device is to be used, the following steps will be performed: measuring the position of the X-ray source S by the X-ray source position measuring device; measuring the position of the shielding disk drive mechanism by the shielding disk driver position measuring device; and measuring the position of each eyeball by the eyeball position measuring device or positioning each eyeball at a predetermined position. The sequence of these steps may be arbitrarily selected.

The computing unit 60 calculates the shielding position SH at which each of the shielding disks 20 should be positioned, based on these results of measurement (data).

Subsequently the computing unit 60 processes and determines the diameter of a shielding disk 20 suitable for each of the eyeballs EB, based on data relating to the size of that eyeball from the eyeball size storing device, data from the X-ray source position measuring device, data from the shielding disk driver position measuring device and data from the eyeball position measuring device.

Based on this determination, a selected circular shielding disk 20 having its proper diameter is set on the supporting portion of the arm 36, 206A or 208A in the shielding disk drive mechanism 30 or 30A by the control unit 100 controlling the shielding disk drive mechanism 30 or 30A. This may be performed in a manual manner.

Subsequently, the computing unit 60 computes or determines the current position of each of the shielding disks 20 in the shielding disk drive mechanism 30 based on the position information about the first and second sliding members 33, from the first and second stepping motors 33A, 35A.

The control unit 100 controls the shielding disk drive mechanism 130 to move each of the shielding disks 20 (or the center thereof) from the current position to the corresponding shielding position SH. In this regard, the X-ray generator 3 may be moved while the X-rays are being emitted from the X-ray source S during use of the X-ray fluoroscopic apparatus 1. Even in such a case, however, the control unit 100 can control, according to the present invention, the shielding disk drive mechanism 30 such that the shielding disk 20 will be moved from the original shielding position SH to a new shielding position SH without discontinuation, in response to movement of the X-ray generator 3.

SECOND EMBODIMENT

The second embodiment of the X-ray shield device of the present invention is different from the first embodiment only in the structures of the shielding position determining means and shielding disk size determining means. Only the different structures will be described, and the structures and operations of the second embodiment similar to those of the first embodiment will be omitted.

Only the components of the second embodiment different from those of the X-ray shield device according to the first embodiment will be described.

Shielding position determining means: A shielding position determining means according to the second embodiment determines a shielding position SH on which an X-ray shielding disk 20 should be centered and at which a line extending centrally through the X-ray source S and a position PP of a projection image of an eyeball EB on the projection plane P, intersects the shielding plate movement plane SMP. The shielding position determining means comprises a shielding disk driver position measuring device, an X-ray source position measuring device, an eyeball image position measuring device for measuring the position of the image of an eyeball EB formed on the projection plane P of the X-ray detector 4 relative to the common reference point CSP, and a computing unit 60 for computing or determining the shielding position SH based on data from the shielding disk drive mechanism position measuring device, data from the X-ray source position measuring device and data from the imaged eyeball position measuring device.

The shielding disk driver position measuring device and X-ray source position measuring device in the shielding position determining means of the X-ray shield device according to the second embodiment are identical with those of the first embodiment. On the other hand, the X-ray shield device of the second embodiment is different from that of the first embodiment in that it has the eyeball image position measuring device and that the computing unit 60 computes the shielding position SH of each shielding disk 20.

Projected eyeball image position measuring device: The projected eyeball image position measuring device comprises a projection plane position measuring device for measuring any point ("projection reference point PSP") in the projection plane P relative to the common reference point CSP, a lateral projected eyeball image position measuring device for measuring the position of an eyeball in the X-Y axis relative to the projection reference point PSP in the projection plane P, and a computing unit 60 for computing the position of the projected eyeball image (or the center thereof) ("projected eyeball image position PP") based on data from the projection plane position measuring device and lateral projected eyeball image position measuring device.

Figure 13:
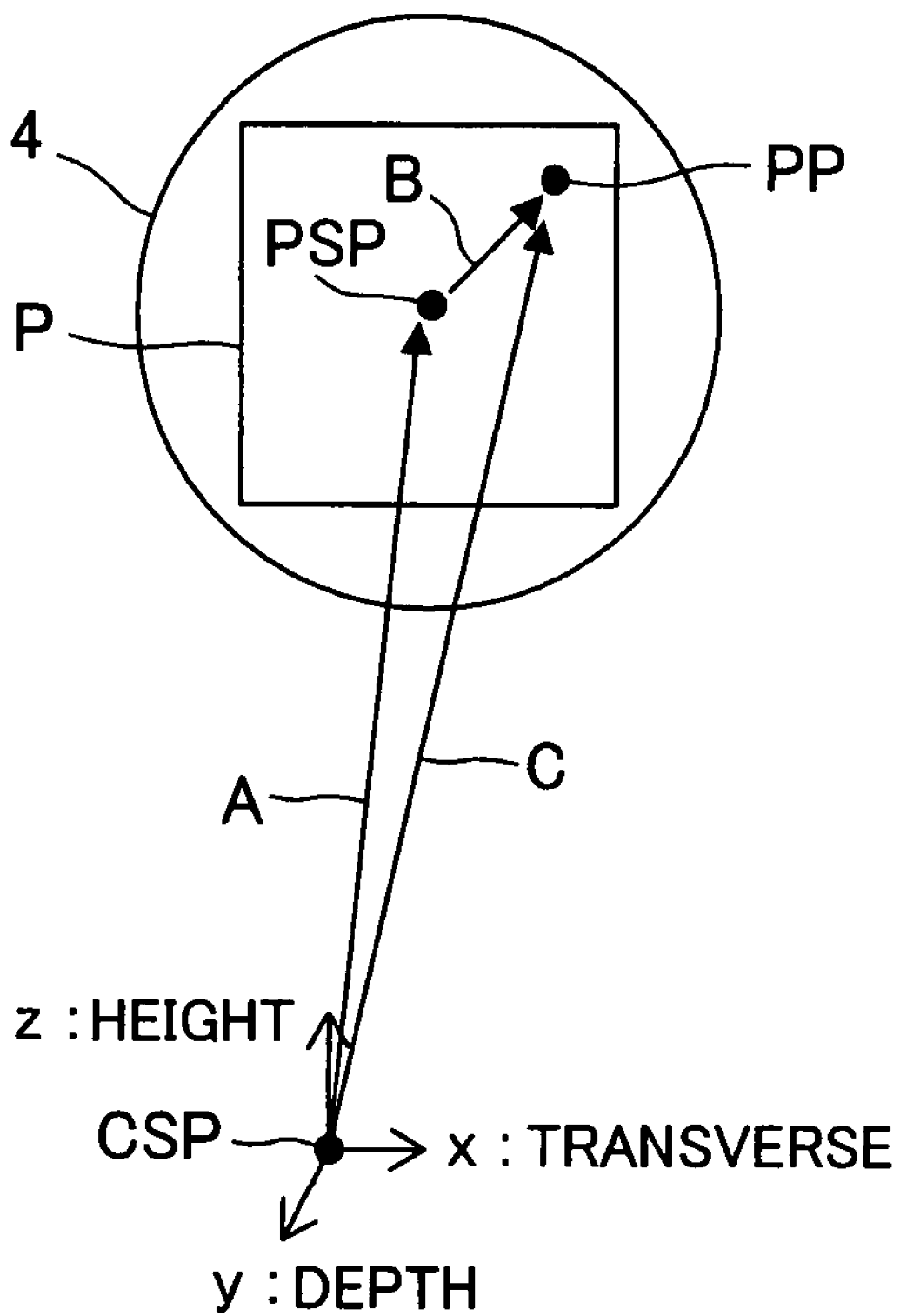
FIG. 13 is a schematic view illustrating the positional relationship between the common reference point CSP, the projection reference point PSP and the projected eyeball image position PP.

FIG. 13 schematically illustrates the relationship between the common reference point CSP, the projection reference point PSP and the projected eyeball image position PP. In this figure, arrows A and C indicate position vectors on the basis of the common reference point CSP while an arrow B indicates a position vector on the basis of the projection reference point PSP.

Projection plane position measuring device: The projection plane position measuring device may be configured by the components as exemplified in the following:

(1) Position output means of the angiographic system 1: If each of the aforementioned motors 6A, 7C, 8A and 8B in the angiographic system 1 is provided with a position output means such as an encoder which can output the positional data of the corresponding movable part moved by the corresponding one of these motors in the angiographic system 1, the projection plane position measuring device may comprise such a position output means, and a computing unit 60 for computing or determining the position of the projection plane P based on the positional data outputted from said position output means.

(2) Position measuring device to be retrofitted: If each of the motors 6A, 7C, 8A and 8B of the angiographic system 1 is not provided with position output means such as an encoder which can output the position data of the corresponding movable part moved by that motor in the angiographic system 1, the projection plane position measuring device may comprise a retrofit position measuring device for measuring the position of the movable part in the angiographic system 1 such as a linear encoder or inclination sensor retrofitted to that movable part and a computing unit 60 for computing or determining the position of the projection plane P based on the positional data from the retrofit position determining device.

In either of the above two cases, the computing unit 60 may be provided in the control unit 100 as shown in FIG. 6 or externally connected to the control unit 100.

Figure 14:
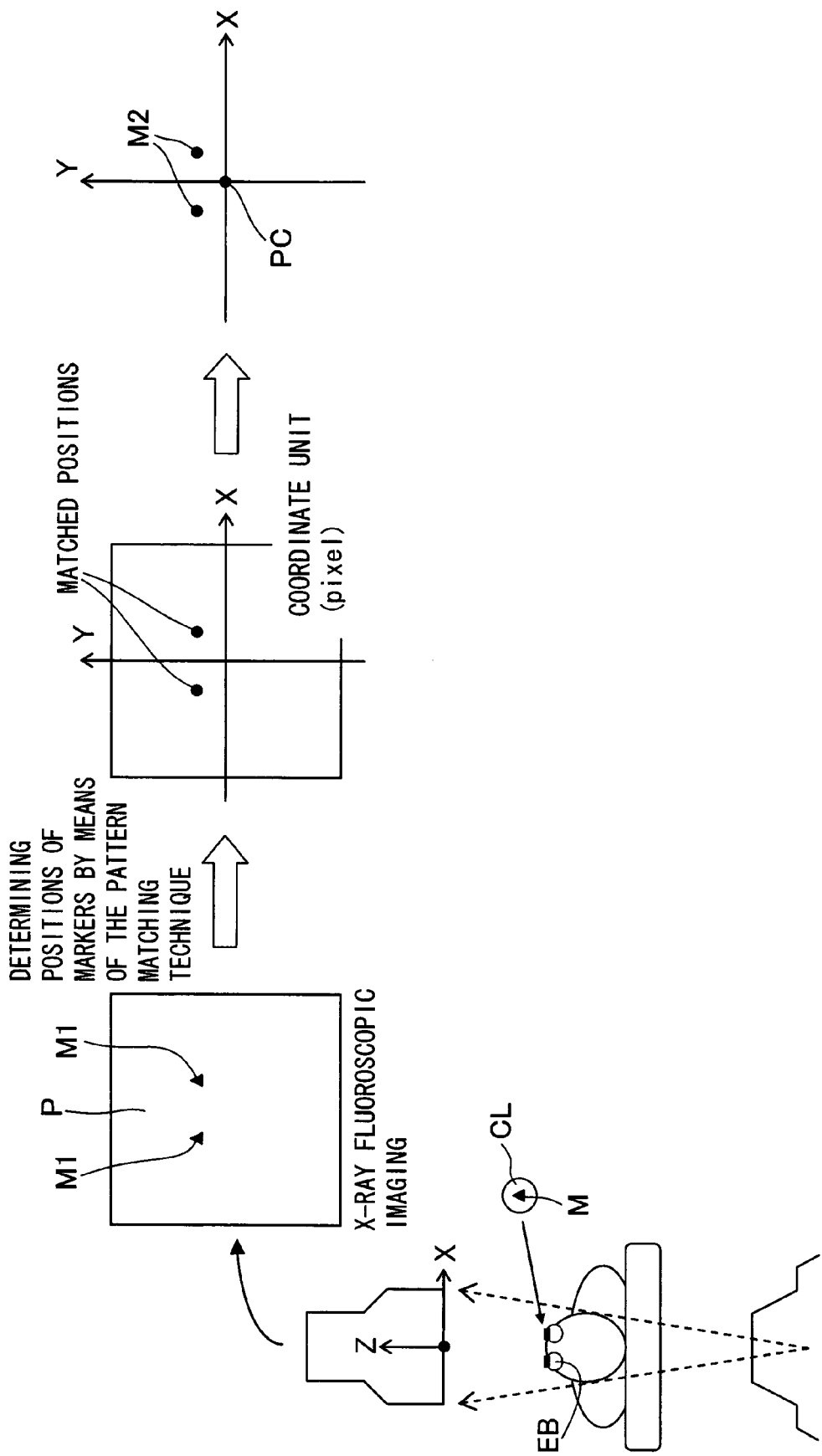
FIG. 14 is a schematic view of a lateral projected eyeball image position measuring device.

Lateral projected eyeball image position measuring device: The lateral projected eyeball image position measuring device may be configured by the components as exemplified in the following:

(1) Contact lens markers: As shown in FIG. 14, the lateral projected eyeball image position measuring device may comprise contact lenses CL each of which is mounted on an eyeball EB and which includes a marker M embedded therein and made of an X-ray shieldable material such as lead or tungsten, means for computing or determining the position M1 of each pixel in the projected image of each of the markers M on the projection plane P of the detector 4 in the angiographic system 1 through the pattern matching technique for image processing when the angiographic system 1 x-rays or visualizes fluoroscopically a patient PA which includes a contact lens CL mounted thereon at each eyeball, and a computing unit 60 for computing the lateral position M2 of the projected image of each marker (i.e., each eyeball EB) in the projection plane P based on the actual size per pixel of the fluoroscopic projected image.

In place of the contact lenses CL, each of the markers M may be mounted on an eye patch (which preferably includes any adhesive material), such an eye patch being then mounted on the eyelid of a patient. The markers may be of any geometric shape, e.g., a star-like shape.

Figure 15:
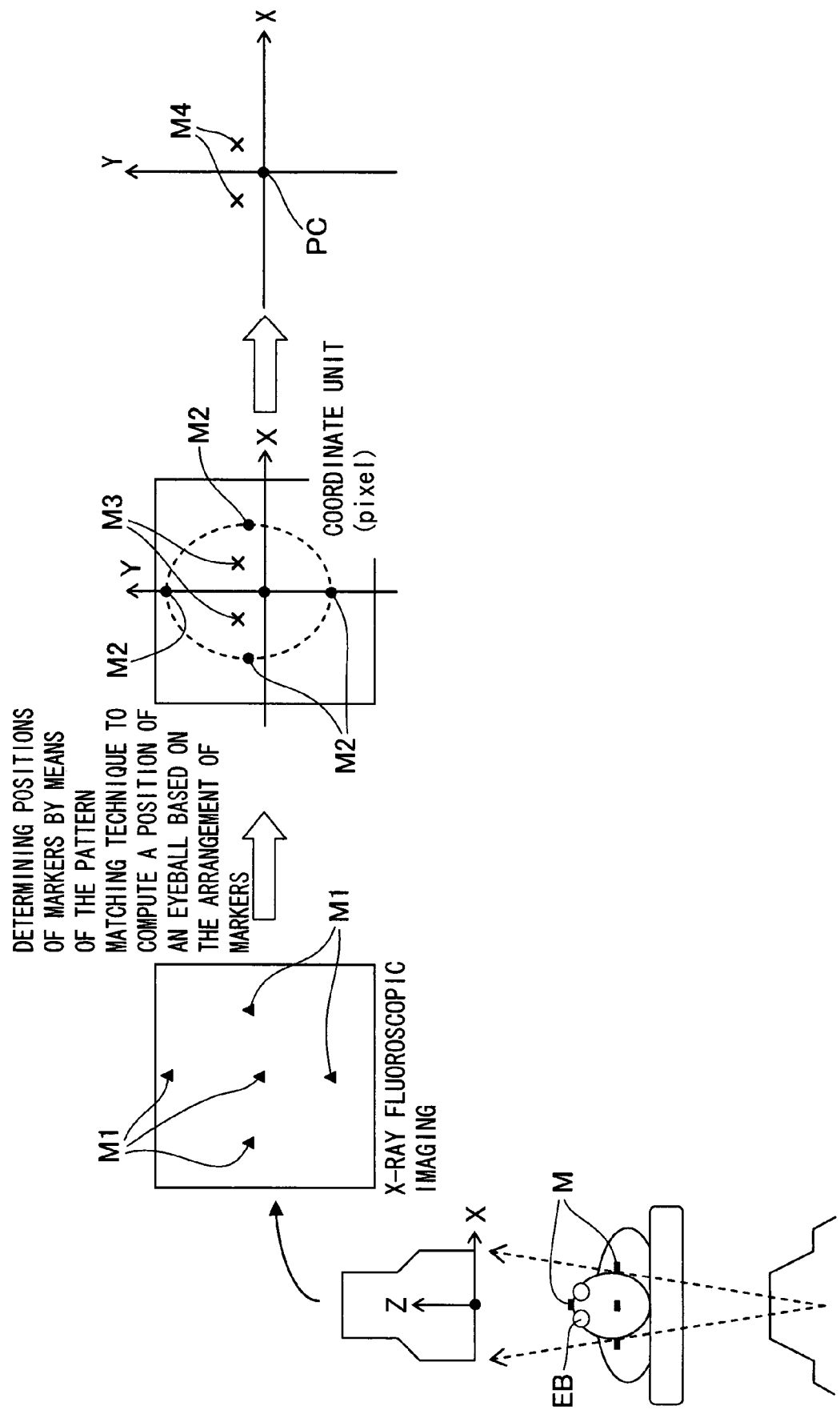
FIG. 15 is a schematic view of another lateral projected eyeball image position measuring device.

(2) Markers: As shown in FIG. 15, the lateral projected eyeball image position measuring device may comprise markers M (preferably including any adhesive material) which are mounted on any distinctive part of the human body such as nose, ear, parietal region or chin other than the eyes (or eyeballs EG) and which are made of any suitable X-ray shielding material, means for computing or determining the pixel positions M1 of the images of the markers M projected onto the X-ray fluoroscope plane P through the pattern matching technique for image processing, and a computing unit 60 for computing or determining an estimated position M3 of each eyeball EB from data relating to the matched position M2 of each of these nose, ear, parietal region and chin and data relating to the relative position between each eyeball EB and any one of the nose, ear, parietal region and chin, the last-mentioned data having been previously stored or accumulated in the storage unit 50 and also for computing the lateral position M4 of the projected image of each eyeball EB in the projection plane P based on the actual size per pixel in the fluoroscopic projected image.

Computing unit: According to the second embodiment, the computing unit 60 is adapted to compute or determine an intersection point (shielding position SH) between the shielding disk movement plane SMP in which the shielding disk 20 is moved and the center line C extending through the X-ray source S and the center PP of the position onto which each eyeball is projected, based on data from the shielding disk driver position measuring device, data from the X-ray source position measuring device and data from the projected eyeball image position measuring device.

Figure 16:
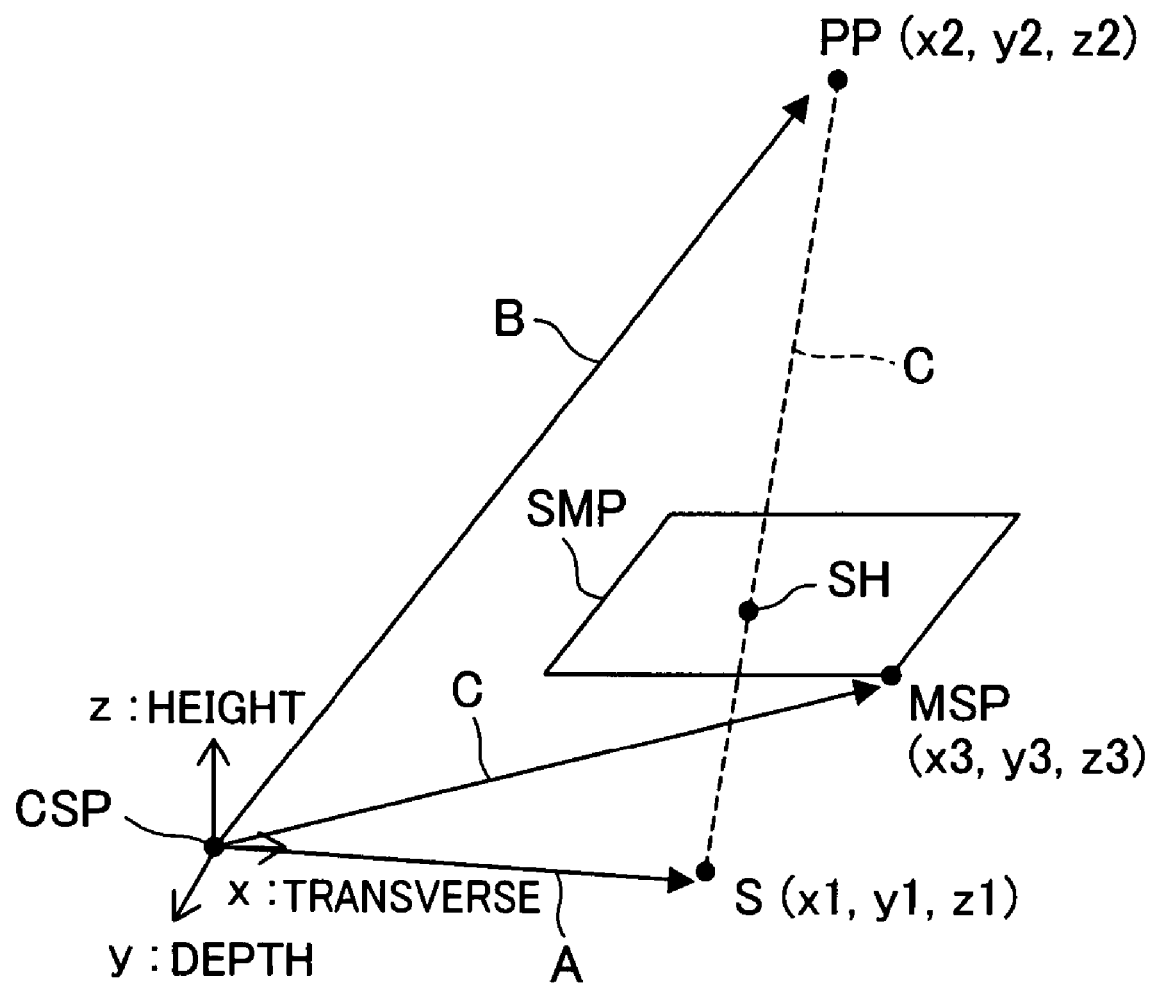
FIG. 16 is a schematic view illustrating the positional relationship between the common reference point CSP, the projected eyeball image position PP and the origin MSP on the shielding disk movement plane SMP.

According to the second embodiment, the computing unit 60 first determines a center line C extending through the X-ray source S and the center PP of the projected eyeball image by use of the following equation (7):

$$x=x1+s(x2-x1), y=y1+s(y2-y1), z=z1+s(z2-z1) \quad (7)$$

where the X-ray source S is at (x1, y1, z1), the position PP of the projected image of each eyeball is at (x2, y2, z2), as schematically illustrated in FIG. 16. In FIG. 16, arrows A, B and C indicate position vectors on the basis of the common reference point CSP.

According to the second embodiment, the computing unit 60 can then compute a shielding disk movement plane SMP using the following equation (8):

$$a(x-x3)+b(y-y3)+c(z-z3)=0 \quad (8)$$

where the position MSP of the shielding disk drive mechanism (or an origin in the shielding disk movement plane SMP) is at (x3, y3, z3), since the normal vectors (a, b, c) of the shielding disk movement plane SMP can be computed from the fact that the shielding disk movement plane is parallel to the projection plane P. By substituting the equation (7) for the equation (8) to solve for "s", the coordinates (position) of the intersection point (i.e., the shielding position SH) can be determined.

Shielding disk size determining means: The shielding disk size determining means according to the second embodiment comprises the shielding position determining means as described above in connection with the second embodiment, a projected eyeball image size measuring device for measuring the size of the projected image of each eyeball EB in the projection plane P of the X-ray detector 4, and a computing unit 60 for computing or determining the size of a shielding disk 20 suitable for that eyeball EB based on data from the shielding position determining means and projected eyeball image size measuring device.

Projected eyeball image size measuring device: The projected eyeball image size measuring device may be configured by the components as exemplified in the following:

(1) Image measuring means in the angiographic system 1: The projected eyeball image size measuring device may be comprise means for measuring the pixel size of the projected image of each eyeball of a patient on the projection plane P of the detector 4 of the angiographic system 1 by use of an image measuring/processing technique utilized by the angiographic system and for measuring the size of the projected eyeball image by multiplying the actual size per pixel of the fluoroscopic projected image and the pixel size of the projected eyeball image together.

(2) Image processing unit to be retrofitted: If the angiographic system 1 does not include an image processing means which can measure the pixel size of the projected image, the projected eyeball image size measuring device may comprise a retrofitted image processing unit for measuring the size of the projected eyeball image by use of an image processing/measuring technique and means for measuring the size of the projected eyeball image by distributing and inputting monitored image signals from the X-ray fluoroscopic apparatus into the image processing unit, measuring the pixel size in the projected eyeball image by use of the image processing/measuring technique and multiplying the actual size per pixel of the fluoroscopic projected image and the pixel size of the projected eyeball image together.

(3) Contact lens markers or Image processing unit using the contact lens markers: The projected eyeball image size measuring device may comprise means for computing or determining the size of a projected eyeball image by comparing the pixel size in the projected image of each eyeball of a patient in the projection plane P of the detector 4 of the angiographic system with the pixel size of the projected image of a contact lens marker mounted directly on each eyeball and having its known size or a contact lens marker mounted near each eyeball and having its known size in the projection plane P.

Computing unit: According to the second embodiment, the computing unit 60 determines the size (diameter) (d) of a shielding disk 20 suitable for each eyeball EB based on the aforementioned data by use of the following equation (9):

$$d = (\text{Distance between the X-ray source position } S \text{ and the shielding position } SH)/(\text{Distance between the X-ray source place } S \text{ and the position } PP \text{ of each of the projected eyeball images}) \times \text{the diameter of a projected eyeball image} \quad (9)$$

In other words, the diameter (d) of the corresponding shielding disk 20 can be determined according to the following equation (10):

$$d = \sqrt{\{(x2-x1)^2 + (y2-y1)^2 + (z2-z1)^2\}} / \sqrt{\{(x3-x1)^2 + (y3-y1)^2 + (z3-z1)^2\}} \times \text{the diameter of a projected eyeball image} \quad (10)$$

where the X-ray source position S is at (x1, y1, z1), the shielding position SH is at (x2, y2, z2) and the position of projected eyeball image PP is at (x3, y3, z3).

The position of projected eyeball image PP relative to the common reference point CSP can be determined based on the projection reference point PSP in the projection plane P provided by the projection plane position measuring device and on the lateral position data of each eyeball EB in the projection plane P provided by the lateral projected image position measuring device.

EXAMPLES

Shielding performance test was performed using an angiographic system available from Toshiba (Trade Name, Circulatory Organ Imager, model/KXO-100G), in which shielding disks 20 each having its diameter of 1.0 cm were respectively mounted on the arm 36 of the shielding disk drive mechanism 30 in the X-ray shield device constructed according to the present invention.

The shielding disks 20 were of two types, one comprising a layered product consisted of an iron sheet having its thickness of 0.5 mm and a lead sheet having its thickness of 3.0 mm (Example 1) and another comprising a layered product consisted of an iron sheet having its thickness of 0.5 mm and a lead sheet having its thickness of 6.0 mm (Example 2). For comparison with these shielding disks 20, the shielding performance test was also performed without shielding disk.

The angiographic system was used with a voltage of 80 kV and a current of 125 mA in an X-ray tube used. Three thermoluminescence dosimeters (170A) were arranged on the right crystalline lens of RANDO™ phantom which was made of a material radiologically equivalent to the human body tissue.

X-rays were irradiated for one minute so that they arrived at the right eye through the back of the head.

In Examples 1 and 2, each of the shielding disks 20 had its center that was on a center line passing through the centers of the tubular lamp and right crystalline lens and that was spaced apart from the tubular lamp by a distance of 45 cm. The center of the right crystalline lens was disposed to be on said center line and to be spaced apart from the tubular lamp by a distance of 92 cm. Furthermore, the distance between the tubular lamp and an image [picture] multiplier was 122 cm.

Test results are shown in Table 1.

TABLE 1

|  | Example 1 | Example 2 | No shielding disk |
|---|---|---|---|
| Right Crystalline Lens | 8.83 | 8.19 | 13.56 |

It could be observed from the results of the aforementioned experiments that the shielding effect relating to the right crystalline lenses each of which was covered with the shielding disk 20 to shield the X-rays was increased by about 35% more than without shielding disk in Example 1 and as much as about 39% more than without shielding disk in Example 2.

The present invention is not limited to the aforementioned embodiments, and various modifications thereto can be made as will be described below.

For example, two or more radioparent arms 36 may be used although the embodiment described in connection with FIG. 5 includes only one radioparent arm 36. In this case, it is preferred that the arms are controlled independently.

Alternatively, a single radioparent arm 36 may be of bifurcated type, for example, so that it can hold two X-ray shielding disks 20. If such a bifurcated arm 36 is to be used for shielding the eyeballs, it is preferable to set the distance between two shielding disks 20, for example, at the average distance between eyeballs.

Furthermore, the shielding disk drive mechanism 30A shown in FIG. 7 can cause two X-ray shielding disks 20 independently to move such that both the eyes of a patient can be shielded against X-rays. Typically, X-rays may be irradiated to one temporal region of a patient PA if the X-ray generator 3 and X-ray detector 4 are located horizontally. In such a case, a single X-ray shielding disk 20 is sufficient to shield one eyeball of the patient against X-rays. If another X-ray shielding disk 20 is used, it may block the irradiation of X-rays to any necessary part. In order to overcome such a problem, two shielding disk drive mechanisms 30A may be provided such that two X-ray shielding disks 20 can be moved in the respective distinct movement planes. In such a case, the two X-ray shielding disks 20 may be positioned on the same path of X-radiation (the same X-rays axis) at the same time. Alternatively, a plurality of shielding disk drive mechanisms 30A may be provided to move three or more X-ray shielding disks 20 in the respective different movement planes.

INDUSTRIAL APPLICABILITY

Although the embodiments of the present invention have been described in connection with the angiographic systems with which the X-ray shield devices according to the present invention may be used, any one of the X-ray shield devices according to the present invention may find application in any radiographic equipments other than the angiographic systems. Furthermore, the X-ray shield devices according to the present invention may be used to shield any radiation other than X-ray.

| LIST OF REFERENCE NUMERALS | |
|---|---|
| 1 | fluoroscopic apparatus |
| 2 | X-ray source |
| 3 | X-ray generator |
| 4 | X-ray detector |
| 9 | bed (support member) |
| 20 | X-ray shielding disk |
| 30 | shielding disk driving mechanism |
| 32A | x-axis guide |
| 33 | first slider |
| 33A | first stepping motor (first motor means) |
| 34 | y-axis guide |
| 35 | second slider |
| 35A | second stepping motor (second motor means) |
| 36 | radioparent arm |
| 100 | control unit |

What is claimed is:

1. An X-ray shield device for use with an X-ray fluoroscopic apparatus for fluoroscopically visualizing a certain site of a subject, comprising an X-ray generator containing an X-ray source, an X-ray detector associated with the X-ray generator and including a projection plane disposed opposed to the X-ray source, and a support member disposed between the X-ray source and the projection plane for supporting the subject, the X-ray shield device being adapted to prevent a specified site of the subject from exposing to the X-ray from the X-ray source, said X-ray shield device comprising:
    at least one X-ray shielding plate positioned between the X-ray source and the support member;
    output means for outputting position data of said support member;
    a shielding plate driving mechanism including a supporting portion for supporting said at least one X-ray shielding plate, said shielding plate driving mechanism being operable to move the shielding plate supported by the supporting portion in a direction transverse to a path of X-ray irradiation;
    shielding position determining means for determining a shielding position where the irradiation from the X-ray should be shielded, wherein the shielding position determining means comprises:
    (a) a position of x-ray source measuring device for measuring the position of the x-ray source S relative to a common reference point;
    (b) a position of shielding plate driving mechanism measuring device for measuring the position of the shielding plate driving mechanism relative to said common reference point;
    (c) a position of non-irradiation site measuring device for measuring the position of said specified site relative to said common reference point based on the position data from the output means and a previously measured distance between the support member and the specified site; and
    (d) a computing unit for computing said shielding position based on data from said X-ray source position measuring device, data from said shielding plate driving mechanism position measuring device and data from said non-irradiation position measuring device; and
    a control unit for controlling operation of said shielding plate driving mechanism to cause movement of said shielding plate to said shielding position in a manner so as to shield said specified site of the subject from the X-ray from the X-ray source of the X-ray generator upon movement of the X-ray generator and the X-ray detector relative to the support member.

2. An X-ray shield device as defined in claim 1, wherein there are a plurality of said X-ray shielding plates, and wherein said supporting portion of the shielding plate driving mechanism is operable to support a selected one of said X-ray shielding plates of different sizes for exchange.

3. An X-ray shield device as defined in claim 2, wherein said shielding position is a position where said X-ray shielding plate is to be centered and at which a line extending centrally through the X-ray source and the specified site of the subject to be shielded from the X-ray irradiation from the X-ray source, intersects a plane in which said shielding plate is moved.

4. An X-ray shield device as defined in claim 3, further comprising a shielding plate size determining means for determining a size of said X-ray shielding plate to be placed at said shielding position that is suitable for said specified site of the subject to be shielded from the X-ray irradiation from the X-ray source.

5. An X-ray shield device as defined in claim 2, further comprising a shielding plate size determining means for determining a size of said X-ray shielding plate to be placed at said shielding position that is suitable for said specified site of the subject to be shielded from the X-ray irradiation from the X-ray source.

6. An X-ray shield device as defined in claim 1, further comprising shielding plate size determining means for determining a size of said X-ray shielding plate to be placed at said shielding position that is suitable for said specified site of the subject to be shielded from the X-ray irradiation from the X-ray source.

7. An X-ray shield device as defined in claim 6, wherein said shielding plate size determining means comprises:
    said shielding position determining means, a size of non-irradiation site storing device for storing data relating to the size of a non-irradiation site of the subject projected onto a plane perpendicular to the center line which passes through the X-ray source and the center of the non-irradiation site, and a computing unit for computing the size of the X-ray shielding plate suitable for the non-irradiation site of the subject based on data provided from said shielding position determining means and data provided from said non-irradiation site's size storing device.

8. An X-ray shield device as defined in claim 7, wherein said shielding plate driving mechanism is adapted to move the X-ray shielding plate along said path of X-ray irradiation.

9. An X-ray shield device as defined in claim 6, further comprising an X-ray shielding plate exchanging means for exchanging said X-ray shielding plate supported by said supporting portion of the X-ray shielding plate driving mechanism for another X-ray shielding plate of different size.

10. An X-ray shield device as defined in claim 6, wherein said shielding plate exchanging means comprises a shielding plate rack for releasably holding more than one X-ray shielding plates of different sizes;

said supporting portion of the X-ray shielding plate driving mechanism is configured to releasably support said X-ray shielding plate;

and said X-ray shielding plate driving mechanism is constructed to move the supporting portion thereof in such a manner that the supporting portion is caused to pass the X-ray shielding plate supported thereby onto said shielding plate rack which can hold that X-ray shielding plate and to receive thereon selected one of X-ray shielding plates held by the shielding plate rack.

11. An X-ray shield plate as defined in claim 10, wherein said control unit is operable to control said X-ray shielding plate exchanging means in such a manner that said supporting portion of the X-ray shielding plate driving mechanism is caused to pass the X-ray shielding plate supported thereby onto said shielding plate rack which can hold the X-ray shielding plate and to receive thereon at least one X-ray shielding plate held by the shielding plate rack whose size is determined by said shielding plate size determining means.

12. An X-ray shield device as defined in claim 1, further comprising a command input unit operatively connected to said control unit.

13. An X-ray shield device as defined in claim 1, wherein said X-ray shield device comprising at least two X-ray shielding plates positioned between the X-ray source and the support member in order to prevent a plurality of specified sites of the subject from exposing to the X-ray from the X-ray source, and at least two shielding plate driving mechanism each operable to move the respective X-ray shielding plate, each of said shielding plate driving mechanisms being adapted to move the respective X-ray shielding plate in a direction transverse to a respective path of X-ray irradiation at a different position on said X-ray irradiation path.

* * * * *